(12) United States Patent
Giese et al.

(10) Patent No.: US 10,308,671 B2
(45) Date of Patent: Jun. 4, 2019

(54) WATER-SOLUBLE DERIVATIVES OF 3,5-DIPHENYL-DIAZOLE COMPOUNDS

(71) Applicants: Max-Planck-Gesellschaft zur Förderung, München (DE); Armin Giese, München (DE); Felix Schmidt, München (DE)

(72) Inventors: Armin Giese, München (DE); Felix Schmidt, München (DE); Christian Griesinger, Göttingen (DE); Andrei Leonov, Göttingen (DE); Sergey Ryazanov, Göttingen (DE)

(73) Assignee: Max-Planck-Gesellschaft zur Forderung, Munich (DE)

( * ) Notice: Subject to any disclaimer, the term of this patent is extended or adjusted under 35 U.S.C. 154(b) by 0 days.

(21) Appl. No.: 16/062,258

(22) PCT Filed: Dec. 14, 2016

(86) PCT No.: PCT/EP2016/081084
§ 371 (c)(1),
(2) Date: Jun. 14, 2018

(87) PCT Pub. No.: WO2017/102893
PCT Pub. Date: Jun. 22, 2017

(65) Prior Publication Data
US 2018/0370997 A1 Dec. 27, 2018

(30) Foreign Application Priority Data
Dec. 14, 2015 (EP) .................................... 15199972

(51) Int. Cl.
*C07F 9/11* (2006.01)
*A61P 25/28* (2006.01)
*A61P 25/16* (2006.01)

(52) U.S. Cl.
CPC ................. *C07F 9/11* (2013.01); *A61P 25/16* (2018.01); *A61P 25/28* (2018.01)

(58) Field of Classification Search
USPC ........................................... 548/112; 514/94
See application file for complete search history.

(56) References Cited

U.S. PATENT DOCUMENTS

2013/0330366 A1    12/2013    Hughes et al.

FOREIGN PATENT DOCUMENTS

WO    WO-2010/000372 A2    1/2010

OTHER PUBLICATIONS

Elumalai et al. Ecotoxicology and Environmental Safety 121, 116-120 (2015) (Year: 2015).*

Jana et al., "Prodrug Design to Improve Pharmacokinetic and Drug Delivery Properties: Challenges to the Discovery Scientists," Current Medicinal Chemistry, vol. 17, 2010, pp. 3874-3908.
Miller, Christa, "Prodrug Approaches for Enhancing the Bioavailability of Drugs with Low Solubility," Chemistry & Biodiversity, vol. 6, 2009, pp. 2071-2083.
Rautio et al., "Prodrugs: design and clinical applications," Nature Reviews, vol. 7, 2008, pp. 255-270.
International Search Report and Written Opinion issued in corresponding application No. PCT/EP2016/081084 dated Feb. 9, 2017.
Extended European Search Report issued in corresponding application No. 15 19 9972.9 dated May 17, 2016.
International Preliminary Report on Patentability issued in corresponding International application No. PCT/EP2016/081084 dated Jun. 28, 2018.

\* cited by examiner

*Primary Examiner* — Nyeemah A Grazier
(74) *Attorney, Agent, or Firm* — Foley & Lardner LLP

(57) ABSTRACT

The present invention is concerned with derivatives of 3,5-diphenyl-diazole compounds, which are effective therapeutic agents for use in treating diseases linked to protein aggregation and/or neurodegenerative diseases such as Alzheimer's disease (AD), Parkinson's disease (PD), and Transmissible spongiform encephalopathies (TSEs) such as Creutzfeldt-Jakob disease (CJD).

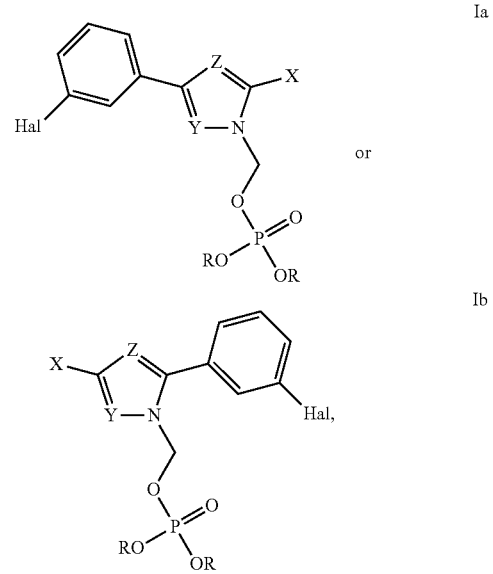

The therapeutic effect is caused by the inhibition of the protein aggregation in the affected tissue, such as the brain. 3,5-Diphenyl-diazole derivatives have been shown to be effective in inhibiting aggregation of proteins but are also characterized by their poor solubility in aqueous solutions. The prodrugs of the invention are modified 3,5-diphenyl-diazole derivatives, which are characterized by their improved solubility in aqueous solutions, and by their increased bioavailability.

18 Claims, 4 Drawing Sheets

WATER-SOLUBLE DERIVATIVES OF 3,5-DIPHENYL-DIAZOLE COMPOUNDS

CROSS-REFERENCE TO RELATED PATENT APPLICATIONS

The present application is a national stage entry of International Application no. PCT/EP2016/081084, filed Dec. 14, 2016, which claims priority to European Patent Application no. 15 19 9972.9, filed Dec. 14, 2015. The foregoing applications are incorporated herein by reference in their entirety.

FIELD OF THE INVENTION

The present invention is concerned with water-soluble derivatives of 3,5-diphenyl-diazole compounds, which are effective therapeutic agents for use in treating diseases linked to protein aggregation and/or neurodegenerative diseases such as Alzheimer's disease (AD), Parkinson's disease (PD), and Transmissible spongiform encephalopathies (TSEs) such as Creutzfeldt-Jakob disease (CJD).

BACKGROUND

A large number of neurological and neurodegenerative diseases are known, many of which are presently not curable. All common neurodegenerative diseases are characterized by the misfolding, aggregation, and/or deposition of specific proteins in the brain. These diseases include medical conditions such as Parkinson's disease (PD), Alzheimer's disease (AD), Transmissible spongiform encephalopathies (TSEs) such as Creutzfeldt-Jakob disease (CJD), senile dementia, AA amyloidosis, arteriosclerotic dementia, Huntington's disease (HD), cerebral thrombangitis obliterans, dementia with Lewy bodies (DLB), multiple system atrophy (MSA) and many others. Type 2 diabetes is yet another disease whose pathogenesis involves ordered protein aggregation.

In the case of TSEs, the misfolded protein, which forms aggregates, is called "prion", which is derived from "proteinaceous" and "infectious". Therefore TSEs are also called prion diseases. The central event in the pathogenesis of TSEs is the conversion of the cellular prion protein $PrP^C$ into the pathological $PrP^{Sc}$ isoform, which accumulates into large protein aggregates. Prions propagate by transmitting a misfolded protein state. When a prion enters a healthy organism, it induces existing, properly folded proteins to convert into the disease-associated, prion form. These newly formed prions can then go on to convert more proteins themselves; this triggers a chain reaction that produces large amounts of the prion form. All known prions induce the formation of an amyloid fold, in which the protein polymerizes into an aggregate consisting of tightly packed beta sheets. Amyloid aggregates are fibrils, growing at their ends, and replicating when breakage causes two growing ends to become four growing ends. This altered structure is extremely stable and accumulates in infected tissue. The propagation theory described for the prion protein may also apply to amyloid formation in other protein misfolding disorders (PMDs).

Another class of neurodegenerative diseases, the so-called synucleinopathies are characterized by intracellular accumulation of protein aggregates, oligomers, protofibrils and fibrils, containing mainly α-synuclein. In the cases of synucleinopathies it is believed that the pathological effects on nerve cells are induced by the formation of oligomeric aggregates of α-synuclein and the subsequent formation of membrane pores. Examples of synucleinopathies are Parkinson's disease, dementia with Lewy bodies (DLB) and multiple system atrophy.

In fact, protein conformation changes associated with the pathogenesis of most PMDs result in the formation of abnormal proteins that are rich in β-sheet structure, partially resistant to proteolysis, and have a high tendency to form larger-order aggregates, similar to prions. Amyloid formation depends on the slow interaction of misfolded protein monomers to form oligomeric nuclei, around which a faster phase of elongation takes place. The ability of oligomeric species to seed their own growth is analogous to the self-propagating activity of prions.

These oligomers that occur during the aggregation are described in literature as to be the main toxic agent leading to cell dysfunction and cell death. One possible mechanism leading to cell death is membrane perforation caused by the protein aggregates. To treat the disease caused by the protein aggregation in the tissue of the patient, the protein aggregation has to be prevented, decreased or, at best, removed from the tissue.

This can be achieved in the case of prion diseases by a therapeutic approach targeted at interfering with the formation and amplification of the infectious protein ($PrP^{Sc}$). Evidence derived from cell culture and in vivo studies suggests that once formation of $PrP^{Sc}$ is inhibited, clearance of $PrP^{Sc}$ can take place. Thus, this therapeutic strategy can also be effective late in the incubation period and even after manifestation of clinical signs of disease, which is essential to be of use in addressing human prion disease.

There are a number of compounds which have been shown to be effective in interfering with $PrP^{Sc}$ amplification in vitro such as acridin derivatives, Congo Red, porphyrins/phthalo-cyanines, Cp-60, beta-sheet breaker peptides and variants of PrP. However, none of these compounds have so far been used successfully for disease treatment or as lead compounds for developing compounds with increased therapeutic potency and pharmacological properties.

In WO2010/00372, compounds were disclosed, which have been shown to be effective in inhibiting aggregation of proteins. A broad screen based on a combination of scanning for intensely fluorescent targets (SIFT) and cellular assays measuring the amount of aggregation of α-Synuclein (PD) and prion protein (CJD). In this screen 3,5-diphenyl pyrazole (DPP) compounds turned out to be a highly active scaffold that could be easily modified by organic synthesis. An array of around 250 compounds in this class was synthesized and the compounds were assessed for oral availability and efficacy in animal models mimicking the various mentioned diseases (AD, CJD, PD). The compound termed "anle138b" having the following structure:

5-(3-Bromophenyl)-3-(3,4-methylenedioxyphenyl)-1H-pyrazole has been identified as being efficacious in modulating the oligomer formation in animal models mimicking Parkinson's disease (PD) (1,2), Alzheimer's disease (AD) (3) and Creutzfeldt-Jakob's disease (CJD) (1,2). Membrane perforation, which could be the mechanism of oligomer induced neurotoxicity, could be shown to be inhibited by anle138b (1).

Since protein aggregation is happening continuously and leads to neurodysfunction and neuronal loss, a neuroprotective treatment would require chronic application of the therapeutic agent. Such a therapy needs to be non-toxic with chronic dosing and at efficacious compound concentrations. The non-toxicity of anle138b under treatment for more than one year has been shown in several mouse models as described above. In order to minimize the necessary oral dose and still reach efficacious compound levels, the therapeutic compound should also be resorbed most efficiently after oral application. It has been shown that to be effective, the therapeutic agent has to be applied per os and subsequently transferred to the gut, where it will be taken up and transported via the bloodstream into the tissue affected by the protein aggregation. Therefore, the compound has to be capable of passing the blood-brain barrier. To be effective, the concentration of the compound in the gut before uptake into the bloodstream has to be sufficiently high.

However, while 3,5-diphenyl-pyrazole (DPP) derivatives have been shown to be effective in inhibiting aggregation of proteins, it has been found that DPP derivatives are also characterized by their poor solubility in aqueous solution. For example, anle138b has a solubility of 0.2 µM in water.

This problem has been addressed in the case of anle138b by diluting the compound in DMSO and dispersing the diluted compound in oil or peanut butter. In DMSO 1 part of anle138b can be dissolved in 2 parts of DMSO. It has been found that resorption from such olive oil/DMSO suspensions is highly efficient. This composition proved to be well tolerated in mice and rats. However, DMSO is not acceptable for oral application in humans. Therefore, alternative applications had to be investigated.

One further approach was to grind dry compound and mix it with the dry mouse/rat food. However, this led to acceptable substance levels only in mice but not in rats. Pharmacokinetic studies showed that rats do not take up the compound from the dry food. This manner of application is also not suitable for a prolonged therapy of a human patient.

A further approach was to modify the therapeutic agent to increase its water solubility. In the prior art, the use of phosphates, esters, or PEG compounds to enhance the solubility of a compound was discussed. It has been found that by combining anle138b with excipients based on PEG/cremophor, an exposure of 25% of the anle138b exposure reached by administration of sery433 can be achieved in rats. However, this approach has several disadvantages. Firstly, volumes in the order of 20:1 excipient/anle138b have to be used and secondly the excipients are not well tolerated by several animal species including humans. For example, Cremophor induces allergic reactions in humans. Furthermore, excipients are expensive and the capsule volumes would be several times larger than the volumes required for an application with a water soluble powder. Furthermore, in clinical practice, compliance might be jeopardized when patients, which suffer from neurodegeneration and therefore often have problems to swallow, need to take a large number of big capsules.

It has been found that increasing the water-solubility of anle138b is specifically challenging because the water-solubility of anle138b is only 0.2 µM (i.e. 70 ng/ml), which is even lower than that of the paradigmatic "brickdust" compound DP-TAT-59 (4). The design of a successful water-soluble derivative of the therapeutic agent is therefore a crucial problem, which cannot be overcome simply by applying the approaches suggested in the prior art.

To design a successful efficacious derivative of the therapeutic agent, the therapeutic characteristics of the agent have to be maintained, while increasing the water-solubility and the bioavailability. For example, the modification of the therapeutic compound has to lead to the therapeutic compound being delivered to the gut in a mainly monodisperse form, so that it can be taken up into the bloodstream. Other positive characteristics of the unmodified therapeutic compound also have to be maintained or even improved. For example, the modified compound has to be stable during storage and during passage from os to gut. It also has to remain non-toxic to be suitable for therapeutic use.

Some common modifications of these compounds have been tested but most of those are either unstable or do not reach useful plasma levels or both.

Thus, a problem to be solved by the present invention is to provide a 3,5-diphenyl-diazole compound suitable for use in treating diseases associated with protein aggregation in a form that is stable, can be applied in a therapeutically useful concentration, and preferably provides a monodisperse solution in the gut. Preferably, the 3,5-diphenyl-diazole compound should be provided in a form which does not require mixing with a large amount of excipients, so that a small volume per dose can be achieved. In particular, it is an object of the present invention to provide a water-soluble form of a 3,5-diphenyl-diazole compound that can be used for oral administration. Furthermore, as the above diseases affect the brain it is also necessary that the effective part of the compound can cross the blood-brain-barrier and can be transported to the brain, i.e. remains stable after the compound has been released in the gut and reaches plasma levels that are sufficient for the treatment.

DESCRIPTION OF DRAWINGS

The invention is also explained with reference to the following figures.

DEFINITIONS

Figure 1:
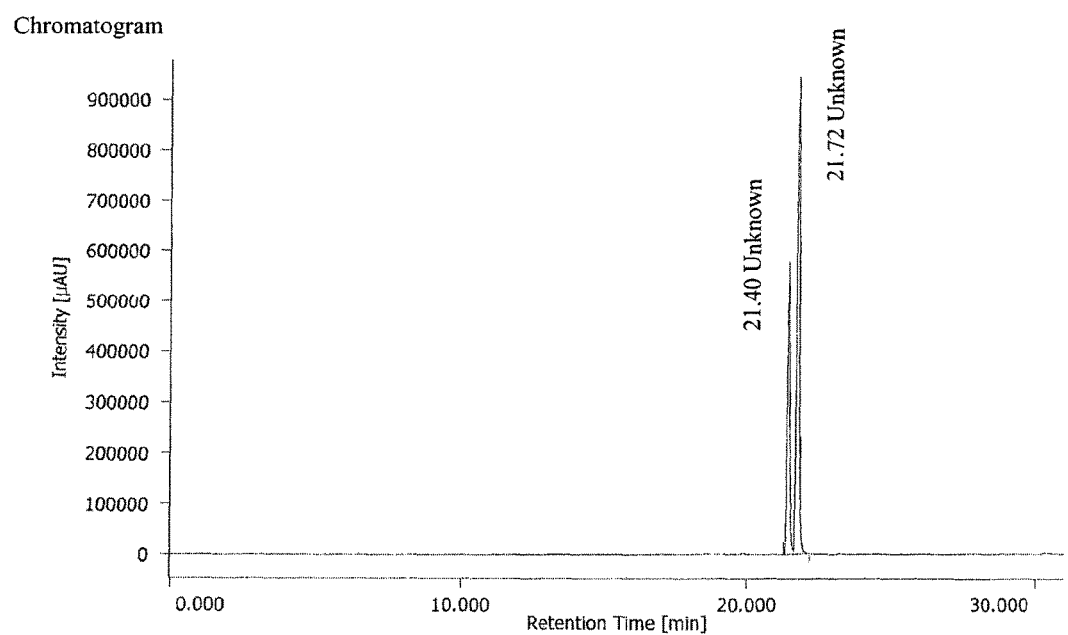
FIG. 1 shows a chromatogram of a HPLC analysis of sery433, a prodrug of anle138b.
Figure 2:
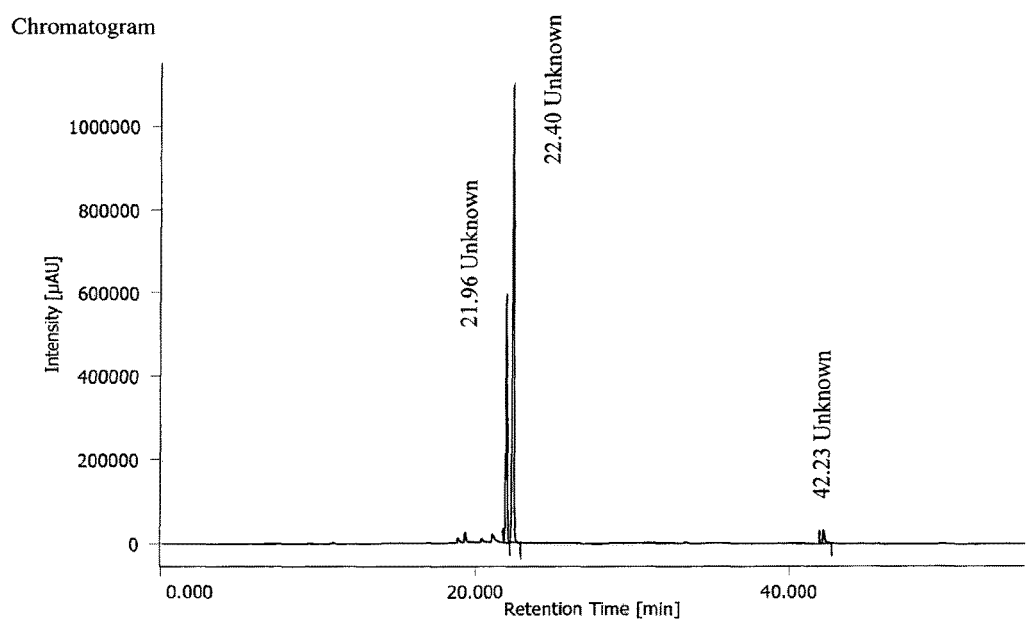
FIG. 2 shows a chromatogram of a HPLC analysis of anle423b, a prodrug of anle253b.

In this description and the claims, reference will be made to a number of terms which shall be defined to have the following meanings:

A "3,5-diphenyl-diazole compound" in the context of the present invention refers to a compound having a diazole core that is substituted by two substituted or unsubstituted phenyl groups in positions 3 and 5 or in positions 2 and 4 or in positions 2 and 5. The diazole core is either derived from pyrazole or from imidazole. In other words, the 3,5-diphenyl-diazole compound of the present invention is in particular a 3,5-diphenyl-pyrazole (DPP) compound or a 2,4-diphenyl-imidazole (DPI) or a 2,5-diphenylimidazole (DPI) compound, wherein the phenyl groups can be substituted or unsubstituted. Whenever a DPP compound is disclosed, it is understood that the disclosure also applies to the corresponding DPI compound, as long as the context allows.

The diazole core of the compounds of the present invention can exist in two tautomeric forms. Each tautomeric form alone as well as a mixture of both is encompassed by the term "diazole".

The term "anle138b" is used to describe a therapeutic agent also known as 5-(3-bromophenyl)-3-(3,4-methylenedioxyphenyl)-1H-pyrazole. The pyrazole ring of the compound exists in two tautomeric forms:

Therefore "anle138b" can be described by the following structural formulae:

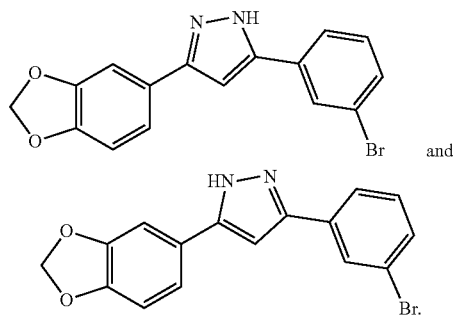

Whenever in the description one of the above mentioned structures is disclosed, the other structure as well as mixtures of both structures are intended to be encompassed. The same applies to other structural formulae describing diazole derivatives of the present invention, for example DPP derivatives of the present invention such as sery335b and anle253b.

The term "disease associated with protein aggregation" is used for all conditions, disorders, or diseases characterized by the presence of an aggregated form of at least one protein or a fragment or derivative thereof, wherein the protein is preferably selected from the group consisting of prion protein, amyloid precursor protein (APP), alpha-synuclein, superoxide dismutase, tau, immunoglobulin, amyloid-A, transthyretin, beta 2-microglobulin, cystatin C, apolipoproteine A1, TDP-43, islet amyloid polypeptide, ANF, gelsolin, insulin, lysozyme, fibrinogen, huntingtin and ataxin and other proteins with a Poly-Q stretch.

The term "prion disease" or TSE is used for all conditions, disorders or diseases that are caused by formation of prions, i.e. proteins that misfold and induce misfolding of other protein molecules. Examples for prion diseases include sporadic and genetic Creutzfeldt-Jakob disease, variant Creutzfeldt-Jakob disease (vCJD), a human disorder caused by the infectious agent of bovine spongiform encephalopathy (BSE), Gerstmann-Straussler-Scheinker syndrome, fatal familial insomnia and kuru. TSEs of other mammals include BSE of cattle, scrapie of sheep and goats, feline spongiform encephalopathy (FSE) of cats, transmissible mink encephalopathy (TME) of minks, exotic ungulate encephalopathy (EUE) of Nyala and Greater Kudu, as well as chronic wasting disease (CWD) of deer and elk.

The term "neurodegenerative disease" encompasses diseases or conditions such as Parkinson's disease (PD), Alzheimer's disease (AD), Transmissible spongiform encephalopathies (TSEs) such as Creutzfeldt-Jakob disease (CJD), senile dementia, AA amyloidosis, arteriosclerotic dementia, Huntington's disease (HD), cerebral thrombangitis obliterans, dementia with Lewy bodies (DLB), frontotemporal dementia, amyotrophic lateral sclerosis, spinocerebellar ataxias, and other Poly-Q diseases, multiple system atrophy (MSA), hereditary cerebral amyloid angiopathy, familial amyloid polyneuropathy, primary systemic amyloidosis (AL amyloidosis), reactive systemic amyloidosis (AA amyloidosis), type II diabetes, injection-localized amyloidosis, beta-2 microglobulin amyloidosis, hereditary non-neuropathic amyloidosis, and Finnish hereditary systemic amyloidosis.

The most prevalent is Alzheimer's disease which affects presently around 7 million patients in Europe, Japan and the US, and whose hallmarks are the aggregation of the protein Aβ to form Alzheimer's plaques and tau protein to form neurofibrillary tangles. Aggregation of tau is also held responsible for progressive supranuclear palsy (PSP), cortico-basal degeneration (CBD) and frontotemporal dementias including Morbus Pick.

Parkinson's disease affects presently around 3.5 million patients in the above listed countries and is characterized by the aggregation of α-synuclein forming Lewy bodies. Multiple system atrophy (MSA) and Lewy Body disease (LBD) are also related to the aggregation of α-synuclein.

Creutzfeldt-Jacob disease is less prevalent as a sporadic form with around 500 new patients per year in Europe. New slaughtering rules have more or less eradicated the occurrence of juvenile CJD. Further neurodegenerative diseases that are related to the aggregation of proteins are Huntington's disease (HD) as well as amyotrophic lateral sclerosis (ALS).

The terms "protein misfolding disorders" (PMD) or proteopathy is used to describe diseases, disorders, or conditions, in which certain proteins become structurally abnormal, and thereby disrupt the function of cells, tissues and organs of the body. Besides the above mentioned prion diseases and neurodegenerative disorders, wherein neurons are the affected cells, other cell types can also be affected by the protein misfolding. One example is type 2 diabetes, wherein the protein amylin, also termed "Islet Amyloid Polypeptide (IAPP), is the major component of diabetes-associated islet amyloid deposits.

The term "prodrug" is used to describe a compound for administration to a patient in a pharmacologically inactive form, which is then converted to an active form through a normal metabolic process. Therefore, a "prodrug" is a precursor chemical compound of a drug. The derivatives of the present invention are used as prodrugs.

DESCRIPTION OF THE PRESENT INVENTION

The present invention is concerned with the provision of a derivative of a therapeutic agent for use in treating a disease associated with protein misfolding/aggregation. The diazole compound derivative of the present invention, also referred to as a prodrug, which is a derivative of a therapeutic agent, is water-soluble, and can be administered in sufficiently high concentration per os to the gut of the patient. The prodrug is stable under normal storage conditions. The prodrug of the present invention is non-toxic at therapeutic concentrations, and is therefore suitable for use in treating patients even for prolonged time periods. The prodrug, i.e. the compound as claimed in claim 1, is therapeutically inactive but will be converted into the bioactive drug within the body of the patient.

The compounds claimed in this application are water-soluble derivatives of 3,5-diphenyl-diazole compounds which can be prepared by the method of the present invention. Preferably, the compound is selected from the group comprising 3,5-diphenyl-pyrazole compounds anle138b, sery335b, sery345, and anle253b.

As outlined above, the diazole compounds of the present invention can exist as tautomers and each of the two tautomers is deducible for all compounds by the skilled person from the name or formula of a compound. Therefore, each tautomer is included as well as mixtures of both tautomers/isomers in any ratio. Furthermore, in the following the structures of one tautomer/isomer of each of the three above mentioned compounds is shown, but the other isomer which is deducible for all compounds by the skilled person is included as well as mixtures of both tautomers/isomers in any ratio.

Anle138b (5-(3-Bromophenyl)-3-(3,4-methylenedioxyphenyl)-1H-pyrazole) is defined by the following structure:

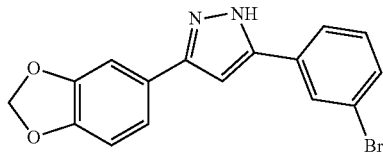 [SMILES: Brc1cccc(-c2cc(-c3ccc4c(c3)OCO4)n[nH]2)c1]

5-(3-Bromophenyl)-3-(3,4-methylenedioxyphenyl)-1H-pyrazole

Sery335b (5-(3-Chlorophenyl)-3-(3,4-methylenedioxyphenyl)-1H-pyrazole) is defined by the following structure:

5-(3-Chlorophenyl)-3-(3,4-methylenedioxyphenyl)-1H-pyrazole

Anle253b, which is even less soluble than anle138b, is defined by the following structure:

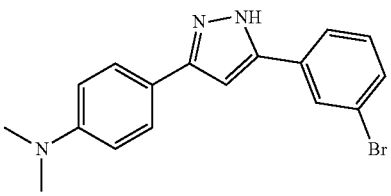 [SMILES: CN(C)c1ccc(-c2cc(-c3cccc(Br)c3)[nH]n2)cc1]

5-(3-Bromophenyl)-3-(4-dimethylaminophenyl)-1H-pyrazole

Sery345 is defined by the following structure:

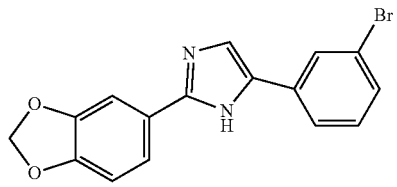 [SMILES: Brc1cccc(-c2cnc(-c3ccc4c(c3)OCO4)[nH]2)c1]

2-(1,3-benzodioxol-5-yl)-5-(3-bromophenyl)-1H-imidazole

These compounds are known for their efficacy in treating diseases involving protein aggregation. Anle138b, for example, has the ability to restore functionality of neurons (1,2). However, these compounds are also characterized by their very low solubility in water which is less desired in medical preparations for oral administration. The present invention now provides derivatives that are stable and suitable prodrugs for oral use in humans.

The inventors surprisingly found that substitution of a methyl phosphate at one nitrogen in the diazole ring of 3,5-diphenyl-pyrazole or 3,5-diphenyl-imidazole compounds improves water solubility without impairing stability. This chemical modification according to the present invention leads to the provision of a prodrug of this valuable therapeutic agent, defined by the following isomeric structures:

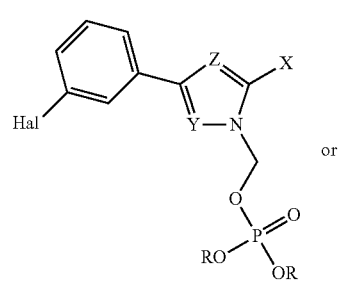

Ia or

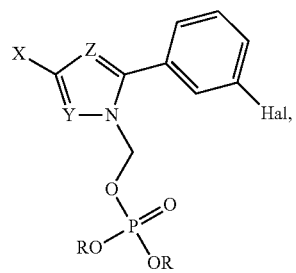

Ib wherein one of Y and Z is N, and the other one is $CR^2$ wherein $R^2$ is selected from hydrogen, $C_{1-4}$ alkyl, $C_{1-4}$ alkyl substituted with at least one halogen; and $C_{6-10}$ aryl, wherein the aryl ring can be optionally substituted by $C_{1-4}$ alkyl or halogen;

wherein either X is

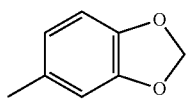

and Hal is halogen selected from chlorine or bromine, or wherein X is

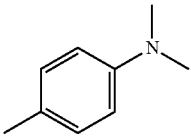

and Hal is bromine; and
wherein each R independently is hydrogen or a cation.

In a preferred embodiment, the compounds of the present invention are defined by the following isomeric structures:

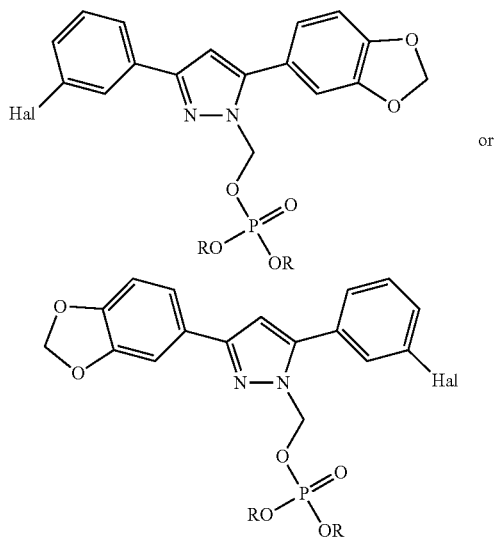

wherein Hal is a halogen selected from chlorine or bromine, and wherein each R independently is selected from hydrogen, or a cation.

In a further preferred embodiment the derivative of the present invention is a prodrug of anle253b with the following isomeric structures:

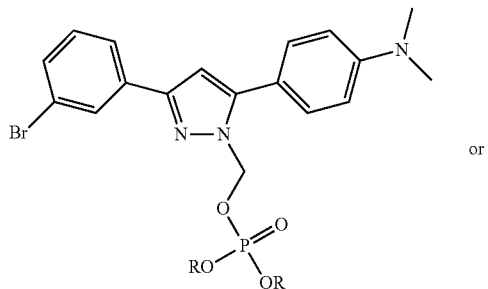

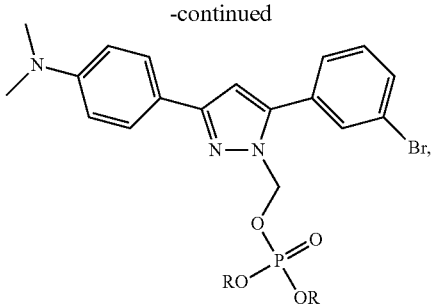

wherein each R independently is selected from hydrogen, or a cation.

The cation can be any cation that is pharmaceutically acceptable for this type of compound. Preferably, the cation is a monovalent cation. Examples are sodium, lithium, potassium, ammonium, in particular sodium. Further examples for groups compatible with the phosphate group of the compounds of the present invention include groups of the structure RR'R"N such as ethanolamine, choline, lysine, meglumine, piperazine, and tromethamine in their protonated form RR'R"NH+. In the compounds of the present invention both R can be hydrogen, both R can be cations (the same or different cations), or one R can be hydrogen and the other one can be a cation. Bivalent cations such as $Ca^{2+}$, $Mg^{2+}$, and $Zn^{2+}$ or trivalent cations such as $Al^{3+}$ are not preferred, as the resulting salts are less water-soluble.

Furthermore, the free acid form (R=H) of the methyl phosphate derivatives of the present invention is also suitable as prodrug.

The present invention also provides a pharmaceutical composition which comprises at least one of the compounds as defined in claim 1. In accordance with the present invention, the term "pharmaceutical composition" relates to a composition for administration to a patient, preferably a mammal, more preferably a human. The pharmaceutical composition of the invention comprises the compounds recited above and, optionally, further molecules capable of altering the characteristics of the compounds of the invention thereby, for example, stabilizing, modulating and/or activating their function. The composition may be in solid, liquid or gaseous form.

Pharmaceutical compositions of the invention may be administered orally, rectally, parenterally, intracisternally, intravaginally, intraperitoneally, topically (as by powders, ointments, drops or transdermal patch), transdermally, by intraarterial injection, intravenously, intraperitoneally, intramuscularly, subcutaneously, bucally, or as an oral or nasal spray. Preferably the pharmaceutical composition are to be administered orally.

With respect to oral administration, the pharmaceutical compositions of the present invention can be provided, for instance, in the form of a tablet, pill, powder (including a powder for dissolution), lozenge, sachet, cachet, elixir, suspension, emulsion, solution, syrup, aerosol, or capsule, preferably in the form of a tablet, pill, or powder (including a powder for dissolution). If desired, the pharmaceutical compositions and in particular the oral formulations mentioned above can be formulated, so that they provide quick, sustained or delayed release and/or release at a certain stage of the passage through the body (e.g., by an enteric coating).

The pharmaceutical compositions as described herein may be formulated using one or more pharmaceutically acceptable additive(s) commonly used in formulation technology, e.g., such as inter alia referred to in Fiedler's "Lexikon der Hilfstoffe" 5th Edition, Editio Cantor Verlag Aulendorf 2002, "The Handbook of Pharmaceutical Excipients", 4th Edition, American Pharmaceuticals Association, 2003. The pharmaceutically acceptable additives may be selected from carriers, diluents or fillers, binding agents/binders, disintegrants, lubricants, glidants, stabilizing agents, surfactants, film-formers, softeners, wetting agents, sweeteners, pigments/colouring agents, antioxidants, preservatives and the like. Suitable carriers, binding agents, disintegrants, lubricants and glidants can e.g. be the ones described in more detail here below as pharmaceutically acceptable additives. Compositions comprising such additives can be formulated by conventional methods.

Suitable carriers include, without limitation, polyols such as mannitol, sorbitol, xylitol; disaccharides such as lactose, sucrose, dextrose and maltose; polysaccharides such as maltodextrine and dextranes; starches such as corn starch; celluloses such as microcrystalline cellulose, sodium carboxy methylcellulose, hydroxypropyl cellulose, hydroxyl ethyl cellulose, hydroxypropyl cellulose or mixtures thereof; cyclodextrines and inorganic agents such as dicalcium phosphate, calcium hydrogen phosphate; hydroxyapatite, tricalcium phosphate, talcum and silica.

Suitable binding agents include, without limitation, hydroxypropylmethyl cellulose (HPMC), hydroxypropyl cellulose (HPC), pregelatinzed starch and combinations thereof.

Suitable disintegrants, include, without limitation, carboxymethylcellulose calcium (CMC-Ca), carboxymethylcellulose sodium (CMC-Na), crosslinked PVP (e.g., crospovidone, Polyplasdone® or Kollidon® XL), alginic acid, sodium alginate, guar gum, cross-linked CMC (croscarmellose sodium, e.g. Ac-Di-Sol®), carboxymethyl starch-Na (sodium starch glycolate) (e.g., Primojel® or Explotab®).

Suitable lubricants, include, without limitation, magnesium stearate, aluminium or calcium silicate, stearic acid, hydrogenated castor oil, talc, glyceryl behenate, sodium stearate fumarate and combinations thereof.

Suitable glidants include, without limitation, colloidal $SiO_2$ (e.g., Aerosil® 200), magnesium trisilicate, powdered cellulose, talc and combinations thereof.

Thus the tablets may contain excipients such as microcrystalline cellulose, lactose, sodium citrate, calcium carbonate, dibasic calcium phosphate and glycine, disintegrants such as starch (for instance, corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, or high molecular weight polyethylene glycols.

Furthermore, the pharmaceutical compositions/dosage forms as described herein may be coated employing film coatings or modified release coatings using coating methods well known to a person of skill in the art using commercially available coating materials such as a mixture of film-forming polymers, opacifiers, colorants and plasticizers.

Lists of further suitable excipients may also be found in textbooks such as Remington's Pharmaceutical Sciences, 18th Ed. (Alfonso R. Gennaro, ed.; Mack Publishing Company, Easton, Pa., 1990); Remington: the Science and Practice of Pharmacy 19th Ed. (Lippincott, Williams & Wilkins, 1995); Handbook of Pharmaceutical Excipients, 3rd Ed. (Arthur H. Kibbe, ed.; Amer. Pharmaceutical Assoc, 1999); the Pharmaceutical Codex: Principles and Practice of Pharmaceutics 12th Ed. (Walter Lund ed.; Pharmaceutical Press, London, 1994); The United States Pharmacopeia: The National Formulary (United States Pharmacopeial Convention); and Goodman and Gilman's: the Pharmacological Basis of Therapeutics (Louis S. Goodman and Lee E. Limbird, eds.; McGraw Hill, 1992), the disclosures of which are hereby incorporated by reference.

The dosage forms as described herein may be formulated in accordance with methods well known to a person of skill in the art, e.g., as described in "Pharmazeutische Technologie", 11th Edition, Deutscher Apotheker Verlag 2010, or "Pharmazeutische Techologie", 9th Edition, Wissenschaftliche Verlagsgesellschaft Stuttgart, 2012.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "therapeutically effective amount" of the pharmaceutical composition for purposes herein is thus determined by such considerations.

Typically, a physician will determine the actual dosage which will be most suitable for an individual subject. The specific dose level and frequency of dosage for any particular individual may be varied and will depend upon a variety of factors including the specific compound employed, mode and time of administration, the severity of the particular condition, and the individual undergoing therapy (the age, body weight, general health, sex, etc.).

The pharmaceutical compositions are preferably provided in unit dosage forms. The compounds of the present invention are typically administered in a therapeutically effective amount. This amount is not particularly limited and a proposed dose of the compounds according to the present invention for administration to a human (of approximately 70 kg body weight) is about 10 to about 1000 mg, preferably about 50 to about 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician.

The composition can comprise one isomeric form of a compound of the present invention or both isomeric forms. The composition can also comprise more than one compound and any of the compounds used in a composition can be either one of both isomers or a mixture thereof. Thus, a pharmaceutical composition for use in treating the above mentioned diseases can comprise one of the isomers or a mixture of both isomers. Both isomeric forms are converted into the bioactive drug within the body.

In one embodiment, the present compounds are provided in dissolved form in an aqueous solution. In the present invention, "dissolved form" means that the present compound is completely soluble at the chosen concentration at room temperature (e.g., 25° C.) in the solvent, so that no undissolved compound can be seen by the naked eye.

It has been found that the disodium phosphate derivative is stable and yields high levels of active compound in brain and blood.

In a preferred embodiment the compound is a disodium phosphate of one of the following structures or a mixture thereof:

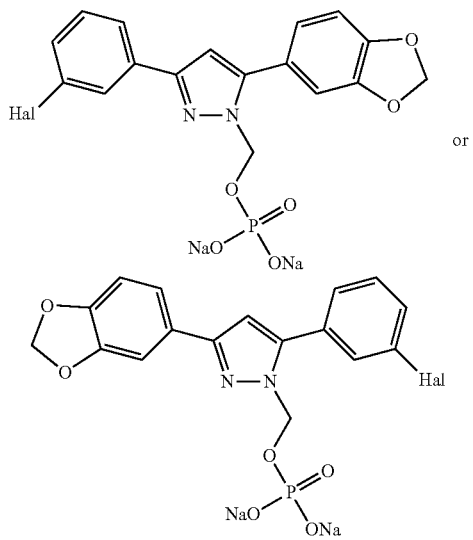

In a preferred embodiment the derivative of the present invention is a disodium methyl phosphate of the therapeutic agent anle138b, i.e. a compound as shown above, wherein Hal is chlorine or bromine. The former derivative is referred to as sery335b, the latter derivative is referred to as sery433. Both can be in the form of one of the isomers or can be a mixture of both isomers. Isomers sery433a or sery433b are shown below:

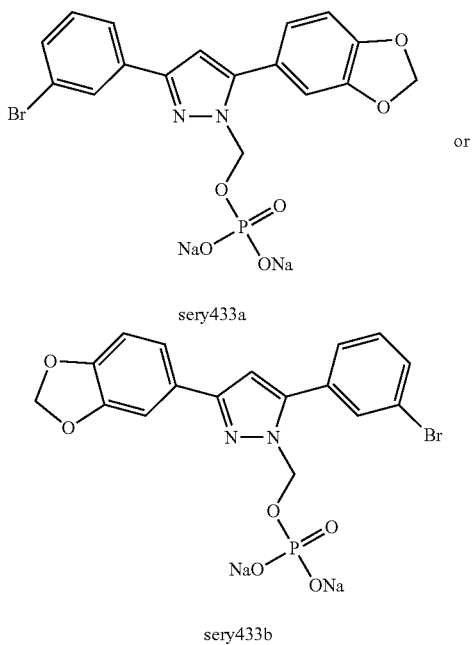

sery433a sery433b

In a preferred embodiment sery433 is an isomeric mixture of sery433a and sery433b, for example with a ratio of sery433b:sery433a=2:3 according to experimental data obtained by 2D-NOESY NMR. Both isomeric forms are converted into the bioactive drug within the body.

It has been surprisingly found that the chemical modification according to the present invention provides a therapeutic compound with the following favourable characteristics:
- efficient conversion to an active form through normal metabolic processes,
- stability under normal storage conditions,
- improved solubility in water,
- improved bioavailability of active compound,
- non-toxicity, and
- stability during the passage from os to gut.

Due to the improved solubility in water as well as the increased bioavailability it is possible to provide the present compounds in significantly smaller volumes of pharmaceutically acceptable additive. This improves patient compliance. Furthermore, it is possible to employ usual pharmaceutically acceptable additives. In contrast thereto, with anle138b special additives (such as cremaphore) were required in order to administer this highly lipophilic compound. Thus, the compounds of the present invention can be favorably used for long-term application. Finally, due to the use of standard additives, the present compounds can be easily provided in standard dosage forms such as a tablet, pill, or powder (including a powder for dissolution) and it is not necessary to provide them in more complicated dosage forms such as capsules.

As can be seen from the examples which are presented below, several other prodrug approaches failed and is thus completely surprising that the above mentioned advantages can be achieved with the presently claimed compounds.

The prodrugs of the invention are modified 3,5-diphenyl-diazole derivatives, which are characterized by their improved solubility in aqueous solutions compared to the parent compounds. With the preferred prodrug sery433 4-fold higher exposure of anle138b is achieved than with anle138b/excipient administration. Thus, disadvantages with intolerance against high dose of additives are avoided and a favorable administration protocol that requires less and/or smaller capsules/tablets can be implemented.

The prodrugs of the present invention are characterized by very high solubility in water (see Example 8). The prodrugs of the present invention are also characterized by their stability in water (see Example 9).

When using the derivatives of the present invention the therapeutically active compound is found in the brain and the blood in therapeutically useful amounts. It is assumed, without being bound by theory, that the active therapeutic compound is released from the prodrug of the present invention by membrane-bound intestinal alkaline phosphatase (IAP) and, thus, close to the gut epithel, where it is directly transferred in the blood stream. Possibly the compound is released in a mainly monodisperse form that can then be taken up from the gut to the blood. The pharmacokinetic characteristics of the prodrugs of the present invention lead to therapeutically useful levels (see Examples 10 and 11) of active compound in the brain and blood in mice and rats. Most importantly, a pharmacokinetic evaluation of the prodrug sery433 of the present invention revealed a significant improvement of exposure, as shown by the AUC and Cmax values. Specifically, the prodrug sery433 administration in comparison to anle138b application in excipient PEG/Cremophor leads to anle138b systemic exposure, either in terms of Cmax and AUC, increased significantly being approximately 4-fold higher in case of the prodrug sery433 (see FIG. 4).

For example, the active compound anle138b is released from the prodrug sery433 at the intestine wall by enzymatic cleavage of the phosphate group from the compound by the membrane-bound intestinal alkaline phosphatase (IAP). Without being bound by theory, it is contemplated that high levels of active compound in blood and brain are possible because the concentration of the active compound at the intestine wall is below the concentration leading to precipitation of the active compound. Furthermore, it is contemplated that the IAP does not release the active therapeutic compound into the lumen of the gut upon cleavage, but holds on to the compound until it has passed onto and through the gut membrane for passive transport into the blood.

EXAMPLES

Preferred embodiments of the invention are outlined in the following examples which should not be interpreted as restricting the scope or spirit of the invention.

Various concepts to solubilize a lipophilic compound exist to make compounds water soluble, i.e. to charge it. A recent summary on such approaches is given by Müller in Chem. Biodiversity (7). In the examples various concepts have been tested, most of which did not result in useful products.

In the following examples the preparation of the derivatives of the present invention and for comparison further approaches of creating a prodrug are illustrated.

Materials and Methods

All starting materials and solvents were purchased from ABCR, Acros, Alfa Aesar, Fluorochem, Sigma-Aldrich or Merck and used as such unless noted otherwise. Melting points were determined on a Stuart Scientific (BIBBY, UK) melting point apparatus using open glass capillares and are uncorrected. Thin layer chromatography (TLC): Macherey-Nagel precoated sheets, 0.25 mm ALUGRAM® SIL G/UV254 plates, detection with UV and/or by charring with 10 wt % ethanolic phosphomolybdic acid reagent followed by heating at 200° C. Flash column chromatography was performed by using Merck silica gel 60 (0.063-0.100 mm). Analytical and preparative high performance liquid chromatography (HPLC) were performed by using a Waters HPLC system with a Waters 996 Photodiode Array Detector. All separations involved a mobile phase of 0.1% trifluoroacetic acid (TFA) (v/v) in water (solvent A) and 0.1% TFA in acetonitrile (solvent B). HPLC was performed by using a reversed-phase (RP) column Eurospher RP 18, 100 Å, 5 µm, 250×4.6 mm (analytical) and 250×16 mm (preparative) at flow rates of 1 mL·min$^{-1}$ (analytical) and 7 mL·min$^{-1}$ (preparative). Electrospray ionization mass spectrometry (ESI-MS) and liquid chromatography/mass spectrometry (LC/MS) analyses were obtained by using a Waters Micromass ZQ 4000 mass spectrometer in conjunction with the Waters HPLC apparatus described above. High-resolution mass spectra (HRMS) were recorded by using an Thermo Scientific LTQ Orbitrap XL hybrid FTMS mass spectrometer and are reported in m/z. NMR spectra were recorded at a temperature of 298 K by using a 400 MHz Bruker Avance spectrometer (Bruker AG, Rheinstetten, Germany) equipped with a TXI HCN z-gradient probe. All spectra were processed by using TOPSPIN2 (Bruker AG, Karlsruhe, Germany). $^1$H NMR chemical shifts (b) are reported in parts per million (ppm) relative to CHCl$_3$ and [D$_5$]DMSO as internal standards. Data are reported as follows: chemical shift, multiplicity (s=singlet, d=doublet, t=triplet, b=broadened, m=multiplet), coupling constants (J, given in Hz), integration. $^{13}$C NMR chemical shifts (δ) are reported in parts per million (ppm) relative to CDCl$_3$ and [D$_6$]DMSO as internal standards. The following experiments were used to record the resonances of the compounds: $^1$H-1D, $^{13}$C-1D NMR spectra and $^{13}$C-APT (attached proton test with a single J-evolution time of $^1/_{145}$ s, spectra are processed such that quaternary and methylene groups have positive sign and methyl and methine groups negative sign). To resolve overlap of resonances and recover undetectable resonances in $^1$H and APT spectra, 2D-[$^{13}$C,$^1$H]-HSQC (heteronuclear single quantum coherence), 2D-[$^{13}$C,$^1$H]-HMBC (heteronuclear multiple bond correlation) and 2D-NOESY were recorded for some compounds. 1,3-Diarylpropane-1,3-diones are presented in the figures as diketones despite the fact that the enol form dominates the spectra.

Example 1: Synthesis of Sery433, a Prodrug of anle138b to be Cleaved by IAP

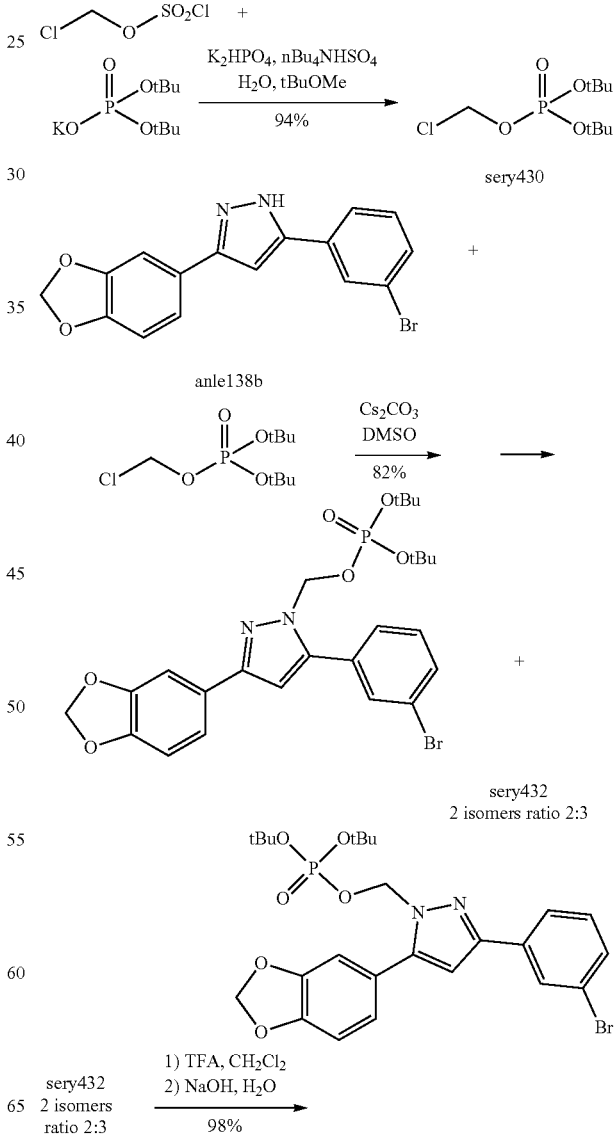

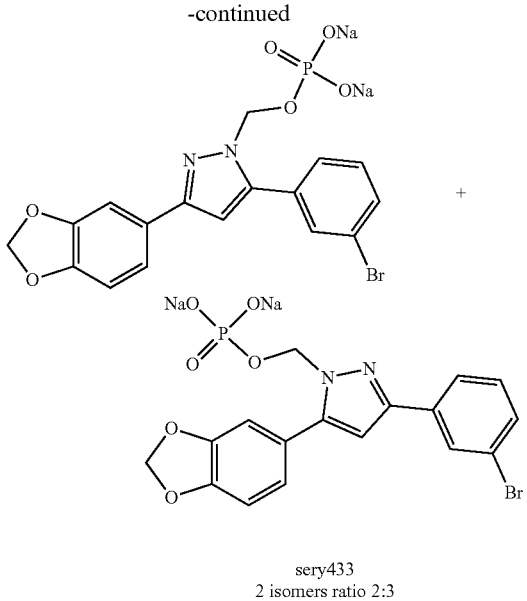

sery433
2 isomers ratio 2:3

Di-tert-butyl chloromethyl phosphate (sery430)

The compound sery433 was prepared according to published protocol (7). To a mixture of di-tert-butyl potassium phosphate (35 g, 141 mmol), $K_2HPO_4 \cdot 3H_2O$ (127 g, 557 mmol), n-$Bu_4NHSO_4$ (4 g, 11 mmol), $H_2O$ (125 ml) and tBuOMe (170 ml) a solution of chloromethyl chlorosulfate (35 g, 212 mmol) in tBuOMe (35 ml) was added dropwise with continuous vigorous stirring in 25 minutes at 0° C. After the addition was completed stirring was continued for 2 hours at room temperature (the reaction mixture was cooled if internal temperature exceeded 30° C.). The reaction mixture was quenched with $H_2O$ (350 ml) and tBuOMe (200 ml), the organic phase was separated, washed with aqueous 1M $K_2HPO_4$ solution (200 ml), water (200 ml), brine (50 ml) and dried over $Na_2SO_4$. After sodium sulfate was filtered, n-$Bu_3N$ (3 ml) was added to the solution and the solution was concentrated under a reduced pressure to provide the product as oil (34.4 g, 94%). An additional portion of n-$Bu_3N$ (3 mL) was added to the product in order to increase the stability during the storage in the freezer (−21° C.).
Sery432

To a mixture of anle138b (1) (25 g, 72.8 mmol), $Cs_2CO_3$ (35.6 g, 109 mmol) in DMSO (200 ml) di-tert-butyl chloromethyl phosphate (28.1 g, 109 mmol) was added in one portion. After stirring at room temperature for 5 hours the reaction mixture was diluted with water (1200 ml) and extracted with diethyl ether (500+200+100 ml). Combined organic fractions were washed with water (500 ml), brine (100 ml) and dried over $Na_2SO_4$. After sodium sulfate was filtered the solution was concentrated under a reduced pressure to provide the product as oil (49.5 g total, 40.8 g sery432, 82%, mixture of two isomers with ratio 2:3). The resulting product also contains 10.5% of sery430 and 7.1% $Bu_3N$ based on $^1H$ NMR spectrum. The product was used in the next step without further purification. Sery432 is the mixture of isomers in ratio 2:3 ($^1H$ NMR).
Sery433

To a cooled solution of sery432 (34.4 g, 60.9 mmol) in DCM (400 ml) TFA (23.5 ml) was added in 5 minutes with continuous vigorous stirring at 0° C. After 2 hours an additional portion of TFA (23 ml) was added and the reaction mixture was stirred at 0° C. for 8 hours. After dilution with cold toluene (300 ml) the reaction mixture was concentrated under a reduced pressure at 0° C., the residue was mixed with cold toluene (300 ml) and concentrated once again at 0° C. (DCM was evaporated at 50-100 mbar, TFA and toluene were evaporated with a high vacuum rotor evaporator). The resulting mixture was diluted with cold acetonitrile (300 ml), and stirred for one hour at 0° C. A white precipitate was filtered off and dried under reduced pressure to provide sery433 in acid form (31.0 g total, 29.0 g of sery433 in acid form and 2 g acetonitrile). To the crude sery433 in acid form 1M aqueous NaOH solution (129 ml, 129 mmol, 2 eq) and water (80 ml) were added, the resulting solution was filleted off (Millipore Express Plus filter) and filtrate was lyophilized to provide disodium salt sery433 (30.0 g, 99%, mixture of two isomers with ratio 2:3) as a white powder.

The two isomers of sery433, a derivative of the present invention, are shown below.

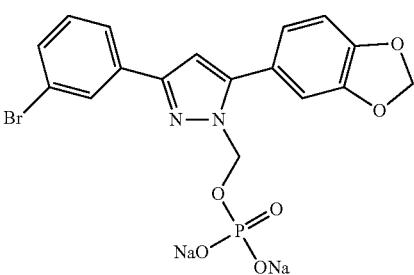

sery433a

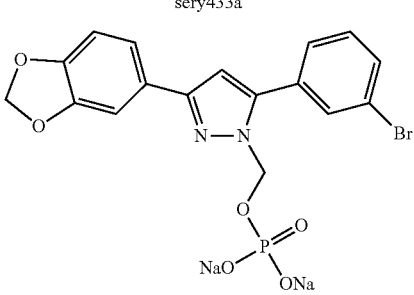

sery433b

Further prodrugs have been prepared:

The stability of compounds in the aqueous solution was determined by NMR. The sample containing a solution of compound (5 mg) in D2O (0.5 ml) was incubated at room temperature for 1 day; 1H spectrums were recorded and analyzed every 12 hours, namely 0 h, 12 h, 24 h time points. Results are summarized in the table below.

| Compound | Result of stability test |
| --- | --- |
| sery433 | stable |
| sery453 | stable |
| anle423b ammonium salt | stable |

Example 2: Synthesis of anle423b (Prodrug of anle253b)

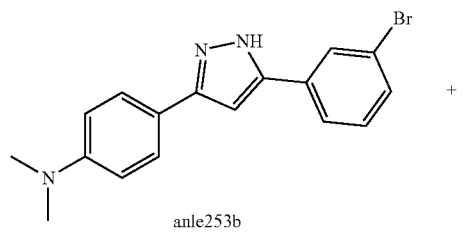
anle253b

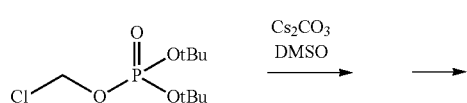
Cs₂CO₃
DMSO

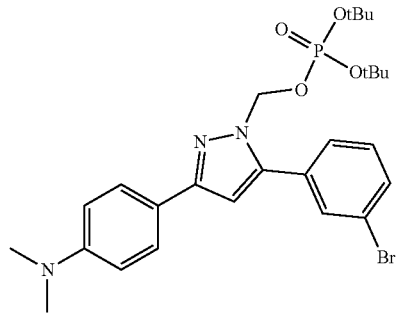

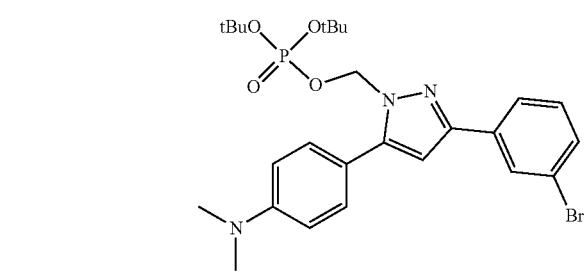
anle423a
2 isomers ratio 2:3

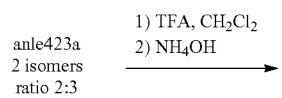
anle423a
2 isomers
ratio 2:3

1) TFA, CH₂Cl₂
2) NH₄OH

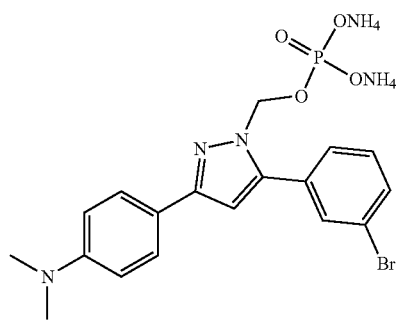

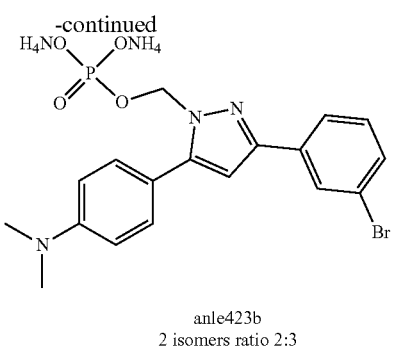
anle423b
2 isomers ratio 2:3

Anle423a

To a mixture of anle253b (500 mg, 1.46 mmol), Cs₂CO₃ (620 mg, 1.9 mmol) in DMSO (5 ml) di-tert-butyl chloromethyl phosphate (525 mg, 1.9 mmol) was added in one portion. After 15 hours of stirring at room temperature completeness of reaction was shown by Thin layer chromatography (TLC) (SiO₂, hexane:EtOAc=2:1, Rf educt 0.33, Rf product 0.18). The reaction mixture was diluted with water (30 ml) and extracted with ethyl acetate (2×15 ml). The combined extracts were washed with water (10 ml), brine (10 ml), dried over Na₂SO₄, and concentrated under reduced pressure to provide the product as oil (1.08 g). The product was used in next step without further purification.

Anle423b (Diammonium Salt)

To a cooled suspension of anle423a (1.08 g) in DCM (10 ml) TFA (2 ml) was added within 1 minute with continuous vigorous stirring at 0° C. and the reaction mixtures was stirred at 0° C. for 8 hours. The mixture was filtered (GHP 0.45 µm), diluted with toluene (10 ml), and concentrated under reduced pressure at 20° C., the residue was mixed with toluene (10 ml) and concentrated once again at 20° C. (DCM was evaporated at 50-100 mbar, TFA and toluene were evaporated with a high vacuum rotor evaporator). The resulting glassy viscous residue was triturated with cold acetone (30 ml), stirred for one hour at 0° C. A white precipitate was filtered off, washed with acetone (10 mL) and dried under reduced pressure to provide anle423b in acid form (448 mg, 0.99 mmol, 68%, mixture of two isomers with ratio anle423ba:anle423bb=3:2 according to 2D-NOESY NMR experiment) as a yellowish powder. To anle423b (diacid, 156 mg, 0.345 mmol) water (3 mL) and 25% NH₄OH (12.6M, 150 µL, 1.89 mmol) were added. The mixture was stirred until dissolution was complete, the resulting solution was frozen and lyophilized to provide diammonium salt anle423b (161 mg, 331 µmol, 96%, mixture of two isomers with ratio anle423ba:anle423bb=3:2) as a yellowish powder.

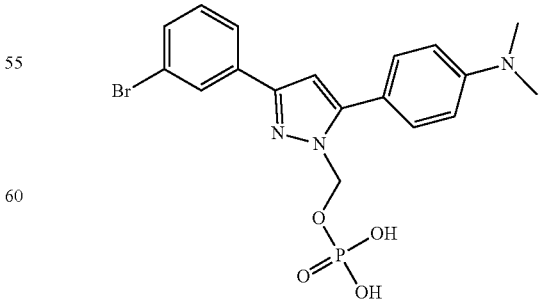
anle423ba

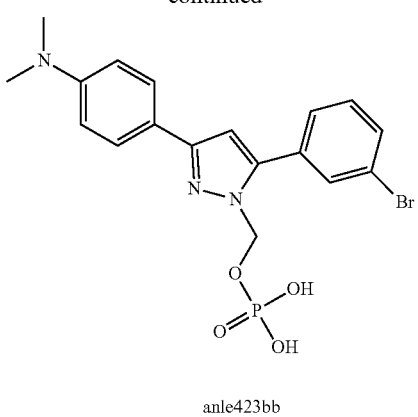

anle423bb

Comparison Example 3: Synthesis of Sery447, to be Cleaved by Esterases

One approach that was tested was the introduction of a group that could be cleaved by esterases and should provide stability via the cation.

Thus, a further potential prodrug of anle138b was synthesized, termed sery447:

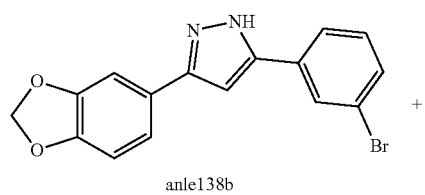

anle138b

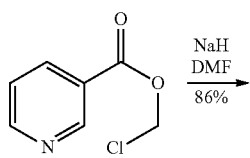

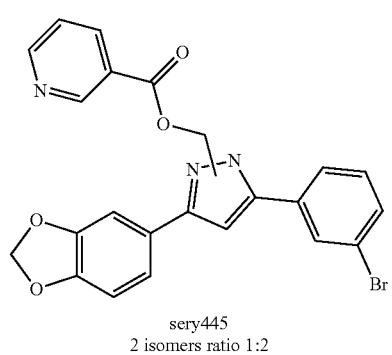

sery445
2 isomers ratio 1:2

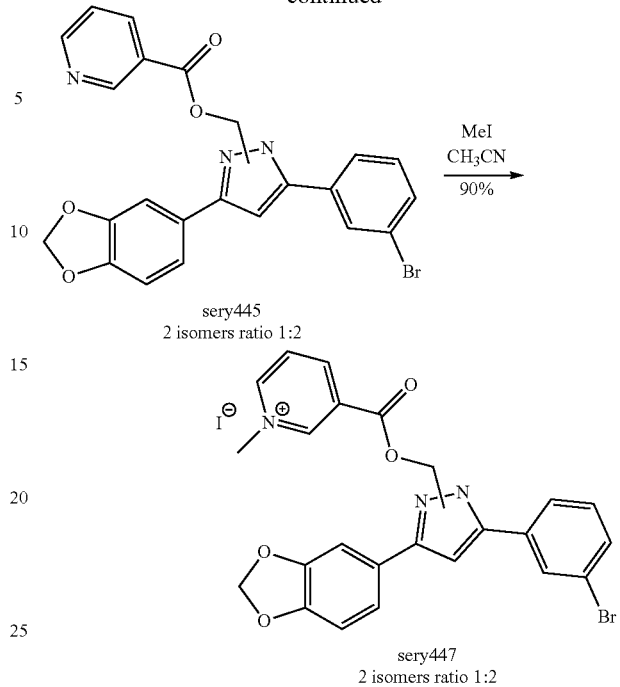

sery445
2 isomers ratio 1:2 sery447
2 isomers ratio 1:2

Nicotinic Acid Chloromethyl Ester

The compound sery447 was prepared according to the published protocol (8) starting from nicotinic acid and purified by flash column chromatography on silica gel (CH$_2$Cl$_2$) to provide nicotinic acid chloromethyl ester (yield 55%) as an yellow oil. TLC (CH$_2$Cl$_2$): RF=0.2.

Sery445

To a suspension of sodium hydride (220 mg, 5.5 mmol; 60% suspension in mineral oil) in anhydrous DMF (10 ml) a solution of anle138b (1.71 g, 5 mmol) in anhydrous DMF (5 ml) was added in 10 minutes with continuous vigorous stirring at room temperature. The mixture was stirred for 30 min at room temperature and then a solution of nicotinic acid chloromethyl ester (0.94 g, 5.5 mmol) in anhydrous DMF (5 ml) was added dropwise. After incubation for 24 hours at room temperature followed by evaporation of DMF under reduced pressure, the residue was dissolved in EtOAc (50 ml), and the solution was washed with water (50 ml), brine (25 ml) and concentrated under reduced pressure. The crude product was purified by column chromatography on silica gel with a gradient elution (EtOAc:hexane, 1:3 v/v to 1:1 v/v) to provide sery445 (2.05 g, 86%) as a solid. Sery445 is the mixture of isomers in ratio 1:2 ($^1$H NMR). TLC (EtOAc: hexane, 1:3 v/v): RF=0.13.

Sery447

A solution of sery445 (1 g, 2.09 mmol) and MeI (1.48 g, 10.4 mmol) in acetonitrile (15 ml) was stirred for 22 hours at room temperature followed by addition of an additional portion of MeI (0.45 g, 3.2 mmol). After stirring for another 24 h at room temperature, the mixture was concentrated under reduced pressure and the residue was resuspended in EtOAc (30 ml). The resulting precipitate was collected by filtration and dried to provide sery447 (1.17 g, 90%) as a yellow solid. Sery447 is the mixture of isomers in ratio 1:1.2 ($^1$H NMR).

Experimental data, however, showed that sery447 had a poor solubility in water (<1 mM). Therefore sery447 was not classified as a suitable prodrug to solve the problems mentioned above.

Comparison Example 4: Synthesis of Sery435, to be Cleaved by Peptidases

In another approach introduction of a group that should be cleavable by peptidases was tested. Stability should be provided via the cation. A further potential prodrug of anle138b was synthesized, termed sery435:

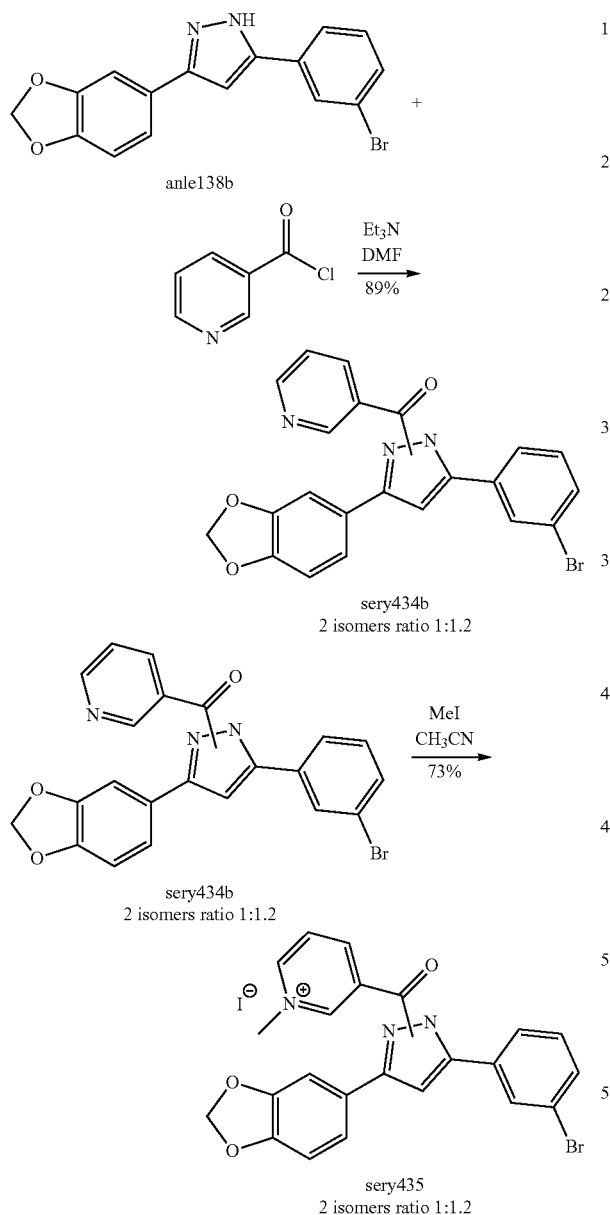

Sery434b

To a suspension of anle138b (1.03 g, 3.0 mmol) and Et₃N (0.81 g, 8 mmol) in DCM (25 ml) nicotinoyl chloride hydrochloride (0.62 g, 3.5 mmol) was added in small portions with continuous vigorous stirring at room temperature. After stirring at room temperature for 4 days, additional portions of nicotinoyl chloride hydrochloride (0.20 g, 1.9 mmol) and Et₃N (0.22 g, 2.2 mmol) were added and the stirring was continued for another 3 days. The mixture was quenched with DCM (25 ml), washed with aqueous 1M phosphate buffer (25 ml, pH 7.0), water (25 ml), brine (10 ml) and dried over Na₂SO₄. The solvent was evaporated under reduced pressure and the residue was purified by flash column chromatography on silica gel (EtOAc:hexane, 1:1 v/v) to provide sery434b (1.2 g, 89%) as a solid. Sery434b is the mixture of isomers in ratio 1:1.2 (¹H NMR). TLC (EtOAc:hexane, 1:1 v/v): RF=0.64.

Sery435

A solution of sery434b (1 g, 2.23 mmol) and MeI (1.5 g, 10.56 mmol) in acetonitrile (12 ml) was stirred for 24 hours at room temperature. Resulting precipitate was collected by filtration and dried to provide sery435 (1 g, 76%) as a yellow solid. Sery435 is the mixture of isomers in ratio 1:1.2 (¹H NMR).

Experimental data, however, showed that sery435 had a poor solubility in water (<1 mM). Therefore sery435 was not classified as a suitable prodrug to solve the problems mentioned above.

Comparison Example 5: Synthesis of Sery453, to be Cleaved by Hydrolysis

In a further approach it was tested if a hydrolyzable group could provide for a water-soluble and stable prodrug, where release of the therapeutic agent anle138b would occur via hydrolysis.

A further potential prodrug of anle138b was synthesized, termed sery453:

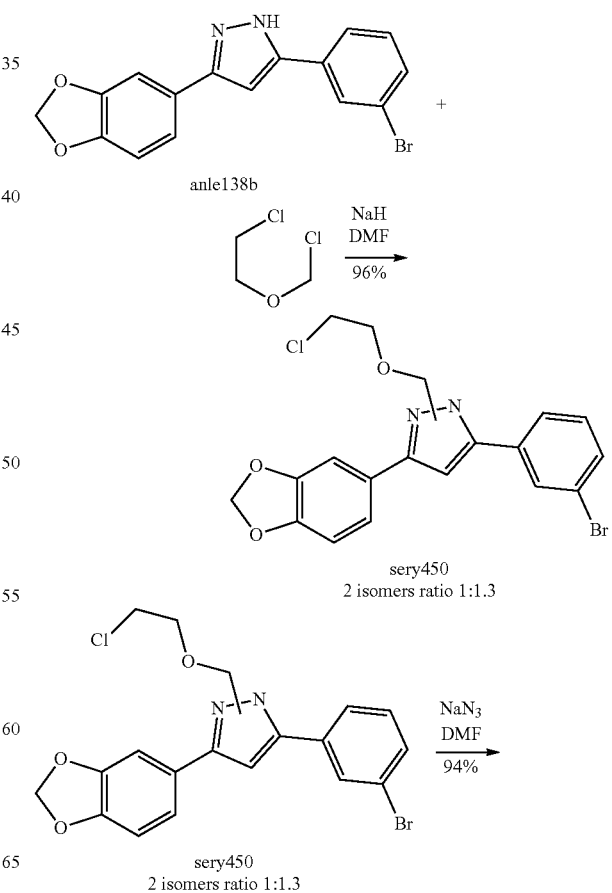

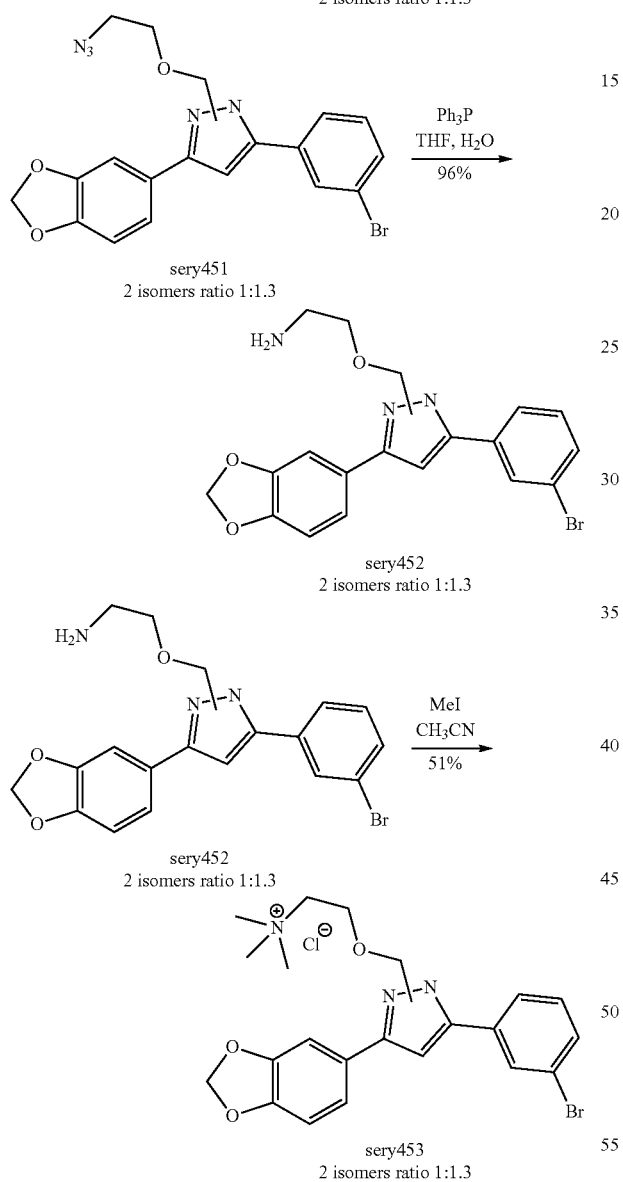

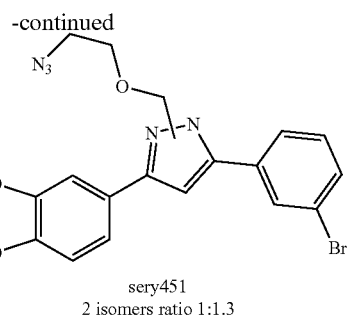

evaporation of DMF under reduced pressure, the residue was dissolved in EtOAc (60 ml), and the solution was washed with water (50 ml), brine (25 ml) and concentrated under reduced pressure. The crude product was purified by column chromatography on silica gel (EtOAc:hexane, 1:3 v/v) to provide sery450 (2.1 g, 96%). Sery450 is the mixture of isomers in ratio 1:1.3 ($^1$H NMR). TLC (EtOAc:hexane, 1:3 v/v): RF=0.58.

Sery451

A mixture of sery450 (1.87 g, 4.3 mmol), NaN$_3$ (2.79 g, 43 mmol), NaI (0.1 g) in DMF (25 ml) was stirred for 15 h at 80° C. and then concentrated under a reduced pressure. The residue was dissolved in EtOAc (90 ml), the organic phase was washed with water (2×50 ml), brine and dried over Na$_2$SO$_4$. After sodium sulfate was filtered the solution was concentrated under a reduced pressure and the resulting mixture was purified by column chromatography on silica gel (EtOAc:hexane, 1:4 v/v) to provide sery451 (1.81 g, 95%). Sery451 is the mixture of isomers in ratio 1:1.3 ($^1$H NMR). TLC (EtOAc:hexane, 1:5 v/v): RF=0.36.

Sery452

A mixture of sery451 (1.67 g, 3.78 mmol), Ph$_3$P (1.49 g, 5.67 mmol), water (2 ml) in THF (25 ml) was stirred for 18 hours at room temperature and then concentrated under reduced pressure. The resulting mixture was purified by column chromatography on silica gel with a gradient elution (CHCl$_3$:MeOH, 30:1 v/v to 9:1 v/v) to provide sery452 (0.38 g, 96%). Sery452 is the mixture of isomers in ratio 1:1.3 ($^1$H NMR). TLC (CHCl$_3$:MeOH, 9:1 v/v):RF=0.19.

Sery453

A mixture of sery452 (1.45 g, 3.48 mmol), MeI (2.97 g, 20.9 mmol), KHCO$_3$ (2.1 g, 21 mmol) in acetonitrile (25 ml) was stirred for 24 hours at room temperature. Insoluble material was filtered off and the filtrate was concentrated under reduced pressure to provide sery453 with iodine as a counterion. Using anion-exchange resin the iodine counterion was replaced by a chlorine counterion to provide sery453 (0.88 mg, 51%) as a white solid. Sery453 is the mixture of isomers in ratio 1:1.3 ($^1$H NMR).

Although, experimental data showed that sery453 had a good solubility in water, this compound did not solve the above-mentioned problems either, as the concentration of anle138b in the brain and blood of mice was relatively low (see Example 10). Sery453 reached levels 8-10 times lower (2 h and 4 h time points) compared to sery433 and therefore was not further considered.

Comparison Example 6: Synthesis of Sery474, to be Cleaved by IAP

A further approach was used in an attempt to provide a water-soluble stable prodrug: a group that could be cleaved by internal alkaline phosphatase was introduced.

A further potential prodrug of anle138b was been synthesized, termed sery474:

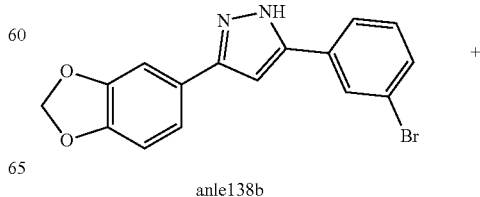

anle138b

Sery450

To a suspension of sodium hydride (220 mg, 5.5 mmol; 60% suspension in mineral oil) in anhydrous DMF (10 ml) a solution of anle138b (1.71 g, 5 mmol) in anhydrous DMF (5 ml) was added in 10 minutes with continuous vigorous stirring at room temperature. The mixture was stirred for 30 min at room temperature and then 2-chloroethyl chloromethyl ether (0.7 g, 5.5 mmol) was added dropwise. After incubation for 30 min at room temperature followed by

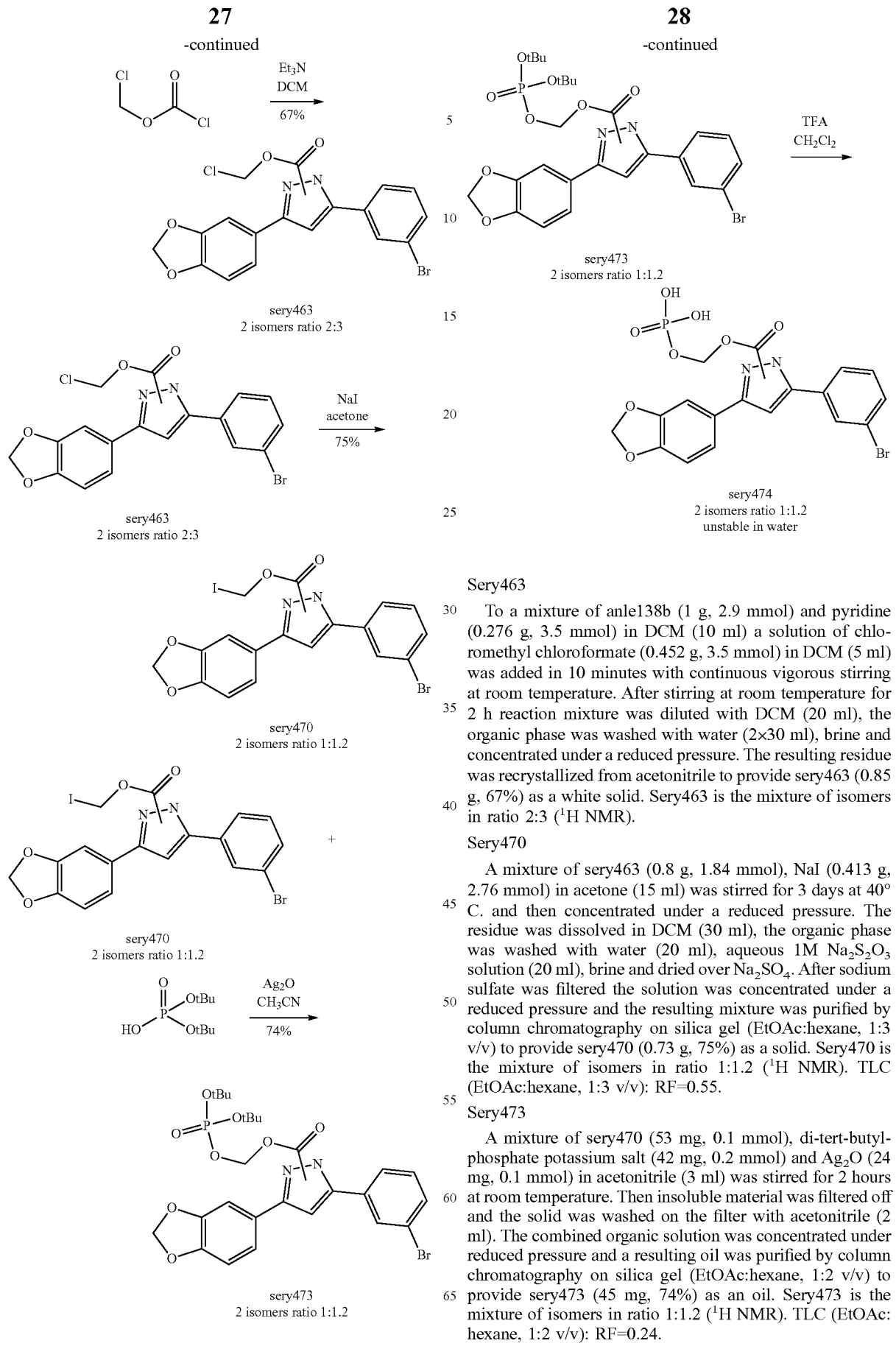

Sery463

To a mixture of anle138b (1 g, 2.9 mmol) and pyridine (0.276 g, 3.5 mmol) in DCM (10 ml) a solution of chloromethyl chloroformate (0.452 g, 3.5 mmol) in DCM (5 ml) was added in 10 minutes with continuous vigorous stirring at room temperature. After stirring at room temperature for 2 h reaction mixture was diluted with DCM (20 ml), the organic phase was washed with water (2×30 ml), brine and concentrated under a reduced pressure. The resulting residue was recrystallized from acetonitrile to provide sery463 (0.85 g, 67%) as a white solid. Sery463 is the mixture of isomers in ratio 2:3 ($^1$H NMR).

Sery470

A mixture of sery463 (0.8 g, 1.84 mmol), NaI (0.413 g, 2.76 mmol) in acetone (15 ml) was stirred for 3 days at 40° C. and then concentrated under a reduced pressure. The residue was dissolved in DCM (30 ml), the organic phase was washed with water (20 ml), aqueous 1M $Na_2S_2O_3$ solution (20 ml), brine and dried over $Na_2SO_4$. After sodium sulfate was filtered the solution was concentrated under a reduced pressure and the resulting mixture was purified by column chromatography on silica gel (EtOAc:hexane, 1:3 v/v) to provide sery470 (0.73 g, 75%) as a solid. Sery470 is the mixture of isomers in ratio 1:1.2 ($^1$H NMR). TLC (EtOAc:hexane, 1:3 v/v): RF=0.55.

Sery473

A mixture of sery470 (53 mg, 0.1 mmol), di-tert-butylphosphate potassium salt (42 mg, 0.2 mmol) and $Ag_2O$ (24 mg, 0.1 mmol) in acetonitrile (3 ml) was stirred for 2 hours at room temperature. Then insoluble material was filtered off and the solid was washed on the filter with acetonitrile (2 ml). The combined organic solution was concentrated under reduced pressure and a resulting oil was purified by column chromatography on silica gel (EtOAc:hexane, 1:2 v/v) to provide sery473 (45 mg, 74%) as an oil. Sery473 is the mixture of isomers in ratio 1:1.2 ($^1$H NMR). TLC (EtOAc:hexane, 1:2 v/v): RF=0.24.

Sery474

A mixture of sery473 (10 mg), TFA (20 mg) in deuterated chloroform (0.7 ml) was placed in the NMR tube and the reaction progression was monitored by NMR. After 6 h incubation at room temperature the $^1$H spectrum demonstrated the reaction completion, the aqueous workout under neutral conditions resulted in decomposition of sery474 leading to formation of anle138b.

Experimental data showed that although sery474 was soluble in water, it could not solve the problem as it did not have sufficient stability. It is assumed that this is due to self-hydrolysis of the acetal function. Therefore sery474 was not classified as a suitable prodrug. Due to the low stability of the sery474 in aqueous solution, the further development was terminated.

Comparison Example 7: Synthesis of Anle380, Based on PEG600, to be Cleaved by Peptidases A common approach when designing a water-soluble and stable prodrug is a derivatisation via PEG600 dicarbonic acid which by itself is miscible in all ratios with water. Thus, a further potential prodrug of anle138b was synthesized, termed anle380:

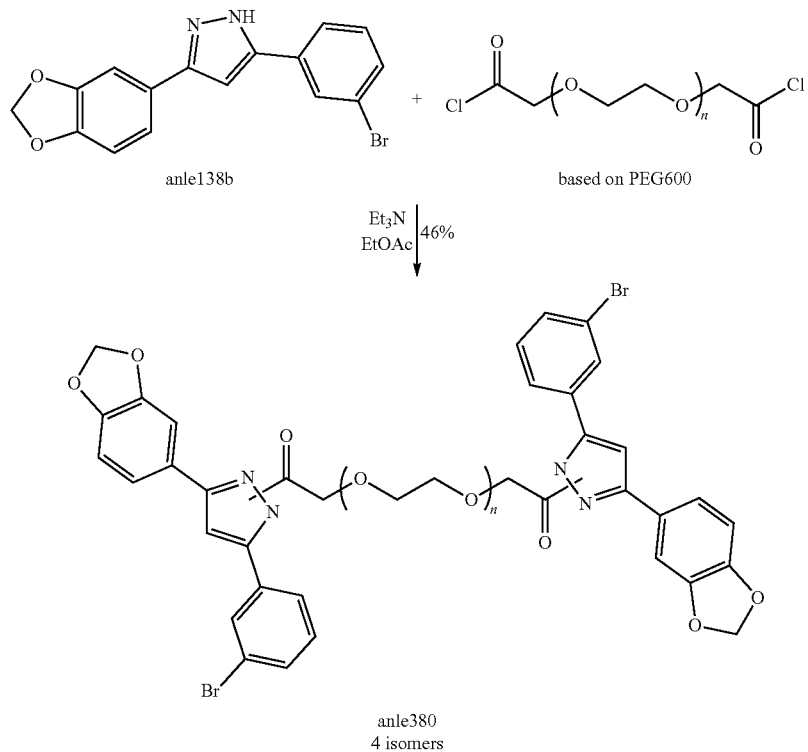

Anle380

A mixture of PEG-based bischloroanhydride (prepared by reaction of corresponding diacid (poly(ethylene glycol) bis (carboxymethyl)ether, average Mn 600) (3 g, 5 mmol) and SOCl$_2$), anle138b (3.43 g, 10 mmol) and Et$_3$N (1.01 g, 10 mmol) in EtOAc (150 ml) was stirred for 24 hours at room temperature. Insoluble material was filtered off; the filtrate was washed with 5% aqueous solution of citric acid (50 ml) and brine. The resulting solution was concentrated under reduced pressure to approximately 20 ml volume and then slowly poured in hexane (150 ml). White precipitate was collected by filtration and dried to provide anle380 (5.8 g) as a white solid. According to LC-MS analysis of this mixture, 4 isomers of desired product are main components, while anle138b and compounds with one heterocycle moiety were detected as main impurities.

Experimental data, however, showed that anle380 had a poor solubility in water (<1 mM). It was unexpected that the PEG600 dicarbonic acid derivative did not reach solubility with the two anle138b moieties attached. Therefore anle380 cannot be used as a suitable prodrug.

Example 8: Water-Solubility Test

The solubility of each compound in the water was evaluated by following protocol. Deionized water (1 ml) was added into glass tube containing 10 mg of compound. After shaking for 10 minutes the sample was visually inspected and formation of solution or suspension was documented. Results are summarized in the table below.

| Compound | Result of solubility test |
| --- | --- |
| sery433 | soluble, clear solution; max. solubility about 150 mg/ml |

-continued

| Compound | Result of solubility test |
| --- | --- |
| sery435 | insoluble, suspension |
| sery447 | insoluble, suspension |
| sery453 | soluble, clear solution; max. solubility about 150 mg/ml |
| anle380 | insoluble, suspension |
| anle138b | insoluble (only 68.6 ng/ml soluble) |

The results show that sery433 and sery453 are approx. 2.19 million times more soluble in water than anle138b.

Example 9: Stability Test

The stability of compounds in the aqueous solution was determined by NMR. The sample containing a solution of compound (5 mg) in D2O (0.5 ml) was incubated at room temperature for 1 day; $^1$H spectrums were recorded and analyzed every 12 hours, namely 0 h, 12 h, 24 h time points. Exemplary results are summarized in the table below.

| Compound | Result of stability test |
| --- | --- |
| sery433 | stable |
| sery453 | stable |
| anle423b ammonium salt | stable |

Therefore, in contrast to the above comparison examples, the derivatives of the present invention are stable. The active compound is released by highly abundant enzyme for cleavage and surprisingly the enzyme does not release the hydrophobic compound into the lumen of the gut but "holds" on to it until it is passed on to the gut membrane for passive transport into the blood.

Example 10: Pharmacokinetic Analysis of Sery433 and Sery453 in Mice

Solutions of sery433 and sery453 as a disodium salt (7.25 mg; eq. 5 mg of anle138b) in sterile Millipore water (50 µl) were applied by gavage to mice (C57/BL6, 77 days of age). Animals were killed by cervical dislocation at time points 1 h, 2 h, 4 h and 8 h after application (two animals per time point). Brains were taken out, washed with 50 mM Tris buffer pH 7.0 and immediately frozen in liquid nitrogen. Samples were stored at −80° C.

Figure 3:
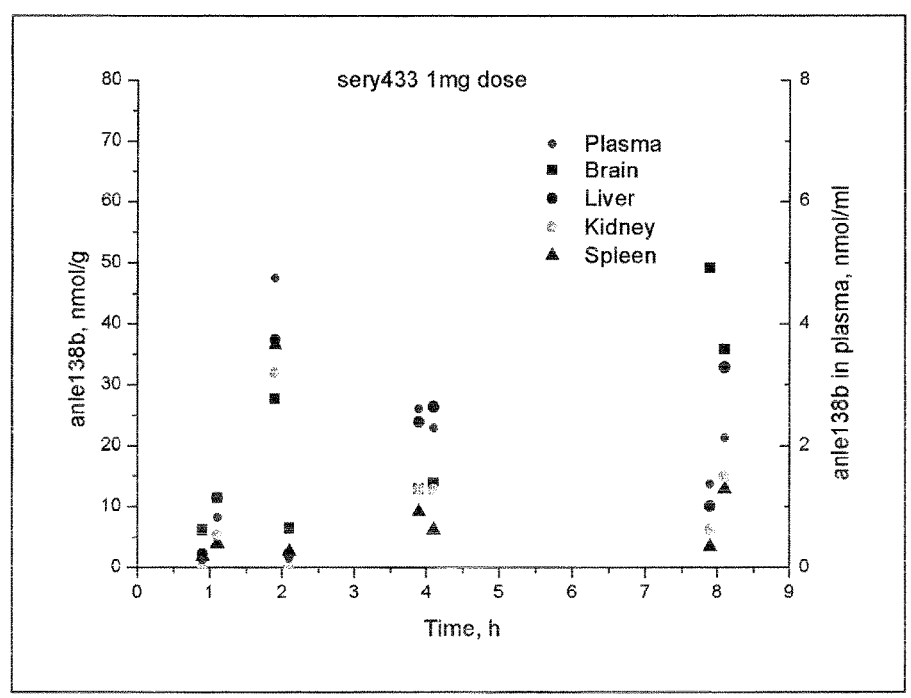
FIG. 3 shows the concentration of anle138b in tissues of mice after application of a dose of 1 mg of the prodrug sery433.

The tissues were thawed at 4° C. prior to use. The tissue was homogenized twice in 5 mL of acetonitrile at maximum speed for 3 minutes using a homogenizer (IKA ULTRA-TURRAX Tube drive workstation, Germany). The homogenate was ultrasonicated at 30° C. for 5 minutes and centrifuged at 5.000×g for 10 minutes. An aliquot (100 µL) of supernatant was injected into HPLC system. Samples were quantified using peak area ratio of compounds to external standard (see FIG. 3).

| Compound | Dose, mg | Animal_No | Time, h | anle138b level in the brain, nmol/g |
| --- | --- | --- | --- | --- |
| sery433 | 1.45 | 1 | 1 | 6.15 |
| | | 2 | 1 | 11.39 |
| | | 3 | 2 | 6.42 |
| | | 4 | 2 | 27.72 |
| | | 5 | 4 | 12.92 |
| | | 6 | 4 | 13.82 |
| | | 7 | 8 | 49.06 |
| | | 8 | 8 | 35.76 |
| sery453 | 1.44 | 1 | 1 | 4.72 |
| | | 2 | 1 | 2.29 |
| | | 3 | 2 | 13.61 |
| | | 4 | 2 | 2.75 |
| | | 5 | 4 | 1.44 |
| | | 6 | 4 | 1.47 |
| | | 7 | 8 | 6.38 |
| | | 8 | 8 | 1.48 |

Example 11: Pharmacokinetic Analysis of Sery433 in Rats

A solution of sery433 as a disodium salt (dose level 10 mg/kg, dose volume 10 ml/kg) in 25 mM phosphate buffer pH 7 was applied by gavage to CD rats. The plasma samples were collected at corresponding time points, frozen in liquid nitrogen and stored at −80° C. The tissues were thawed at 4° C. prior to use. They were homogenized twice in 5 mL of acetonitrile at maximum speed for 3 minutes using a homogenizer (IKA ULTRA-TURRAX Tube drive workstation, Germany). The homogenate was ultrasonicated at 30° C. for 5 minutes and centrifuged at 5000×g for 10 minutes. An aliquot (100 µL) of supernatant was injected into HPLC system. Samples were quantified using peak area ratio of compounds to external standard (see FIG. 3).

Example 12: Pharmacokinetic Analysis of Sery433 in Rats

This study was designed to assess the pharmacokinetics of anle138b and sery433 in male Sprague Dawley rats following single oral administration of anle138b (Phase 1) and sery433 (Phase 2). During Phase 1 and Phase 2 animals received each test compound, appropriately formulated, on one of two separate dose occasions in a cross over design. The dose level was 10 mg/kg for both compounds. The amount of sery433 was not corrected to the amount of anle138b which is present in the prodrug, so that due to the higher molecular weight of sery433 actually a lower amount of active agent was administered.

| | |
| --- | --- |
| Vehicle for anle138b (Phase 1) | PEG 400 (35%) supplied by Sigma Aldrich CAPRYOL 90 (20%) supplied by Gattefosse |
| Storage conditions | Room temperature |
| Vehicle for sery433 (Phase 2) | Phosphate buffer pH 7 (20-25 mM) |
| Storage conditions | Room temperature |

The study was conducted in two phases.

Phase 1: three naïve male CD rats were dosed orally with anle138b at a target dose level of 10 mg/kg.

Phase 2: one week later (wash out period), sery433 at a target dose of 10 mg/kg was administered orally to the same animals.

During each phase an individual serial plasma profile was drawn from each animal over a period of 24 hours after dosing.

Preparation of Oral Dose Formulation (Phase 1)

The vehicle was prepared by weighing Cremophor RH40 (45% of final volume); PEG400 (35% of final volume) and Capryol 90 (20% of final volume). The mixture was stirred and melted at approximately 50° C. (e.g.: thermo-stated bath) for ca. 15 minutes (min) until a clear liquid was obtained. Then test compound was weighed and added to vehicle keep under agitation at 50° C. The mixture was stirred for further 15 min and sonicated for 10 min until a clear (visual inspection) solution was obtained.

Preparation of Oral Dose Formulation (Phase 2)

The vehicle was prepared by weighing Na2HPO4 (3.0 g/L) and NaCl (2.64 g/L); then HCl 1N (1.9 mL to reach pH 7) was added together with ½ of total flask volume of H2O and the mixture was sonicated for 10 minutes. Then the test compound was weighed and added to vehicle under magnetic stirring for approximately 15 min. Then the mixture was sonicated for ca. 5 min and again stirred for 15 min until a clear (visual inspection) solution was obtained.

The nominal concentration of the phosphate buffer was 20 mM.

After oral administration, blood samples were collected from the tail vein of each rat at the following time-points: pre-dose, 0.5, 1, 2, 4, 6, 8 and 24 hours after dosing.

Figure 4:
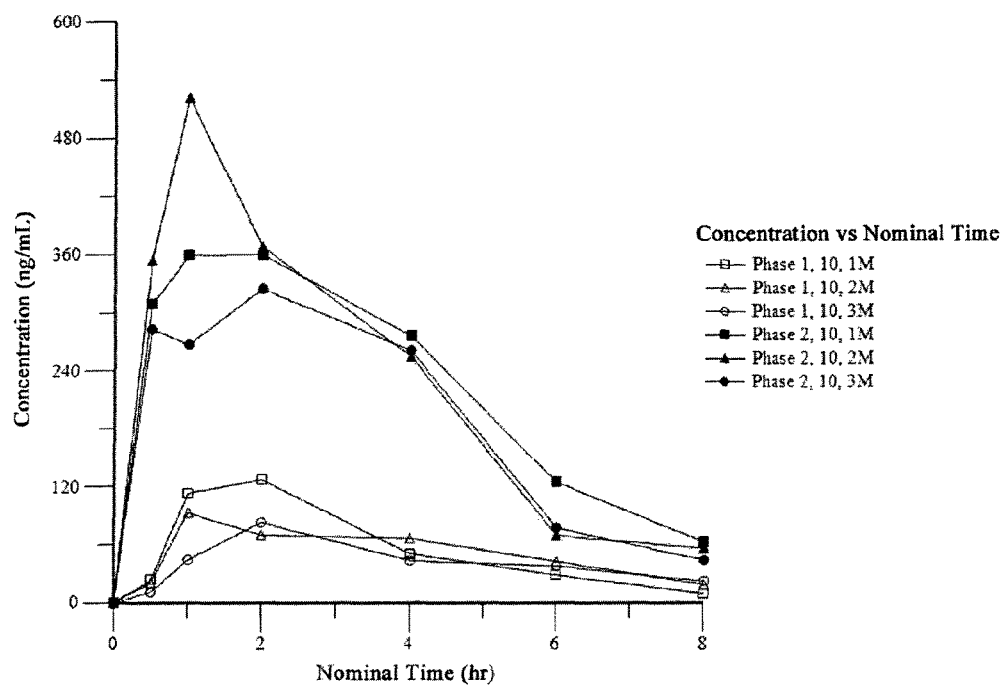
FIG. 4 shows the concentration over time of anle138b in plasma samples of rats after application of the prodrug sery433. In the experiment, a single oral dose of anle138b in PEG/Cremophor ("Phase 1") and sery433 in aqueous solution ("Phase 2") at a nominal dose of 10 mg/kg were administered to male Sprague Dawley Rats. The experiments were conducted with three rats which are identified as "1M", "2M" and "3M".

The results are shown in FIG. 4. As can be seen, the plasma concentrations of anle138b after administration of sery433 were much higher than the corresponding plasma concentrations of anle138b after administration of anle138b as such.

REFERENCES

[1] J. Wagner et al., "Anle138b: a novel oligomer modulator for disease-modifying therapy of neurodegenerative diseases such as prion and Parkinson's disease", Acta Neuropathol. 125, 795-813 (2013)
[2] J. Levin et al., "The oligomer modulator anle138b inhibits disease progression in a Parkinson mouse model even with treatment started after disease onset" Act. Neuropath. 127, 779-780 (2014)
[3] J. Wagner, et al, "Reducing tau aggregates with anle138b delays disease progression in a mouse model of tauopathies" Act. Neuropathol (2015), in print (doi: 10.1007/s0041-015-1483-3)
[4] J. Rautio et al., "Prodrugs: design and clinical applications" Nat. Rew. Drug Disc. 7, 255-270 (2008)
[5] A. H. Burstein, D. Cox, B. Mistry, N. Eddington "Phenytoin pharmacokinetics following oral administration of phenytoin suspension and fosphenytoin solution to rats" Epilepsy Res. 34:129-133 (1999)
[6] T. Heimbach et al., "Enzyme-mediated precipitation of parent drugs from their phosphate prodrugs" Int. J. Pharm. 261, 81-92 (2003)
[7] C. E. Miller, "Prodrug approaches for enhancing the bioavailability of drugs with low solubility" Chem. Biodiversity 6, 2071-2083(2009)ato, K. et al. Composition containing chloromethyl phosphate derivative with improved stability and method for producing the same. EP2133355A1 (2009).
[8] Bodor, N. S. Redox systems for brain-targeted drug delivery. EP0327766A2 (1990).

The invention claimed is:
1. A compound defined by one of the following isomeric structures Ia and Ib

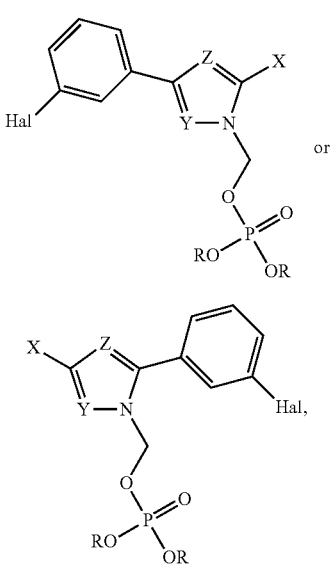

wherein one of Y and Z is N, and the other one is $CR^2$;
wherein $R^2$ is selected from the group consisting of hydrogen, $C_{1-4}$ alkyl, $C_{1-4}$ alkyl substituted with at least one halogen; and $C_{6-10}$ aryl, wherein the aryl ring is unsubstituted or substituted by $C_{1-4}$ alkyl or halogen;
wherein either X is

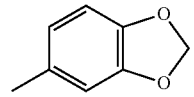

and Hal is halogen selected from chlorine or bromine, or
wherein X is

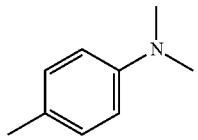

and Hal is bromine; and
wherein each R independently is hydrogen or a cation.
2. The compound of claim 1, wherein Y is N and Z is —CH—.
3. The compound of claim 1 which is

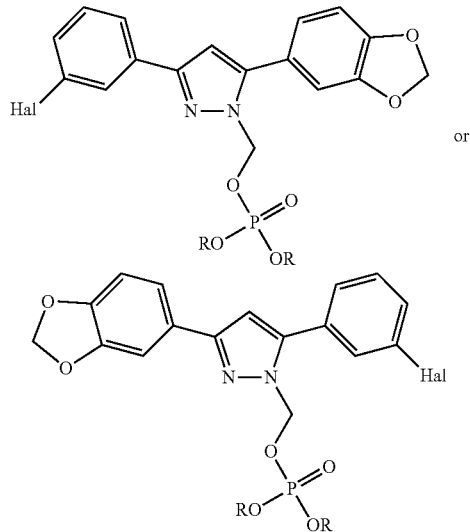

wherein Hal is a halogen selected from chlorine or bromine, and wherein each R independently is selected from hydrogen, or a cation.
4. The compound of claim 1, wherein at least one R is a cation chosen from sodium, lithium, potassium, ammonium, or protonated forms of ethanolamine, choline, lysine, meglumine, piperazine, and tromethamine.
5. The compound of claim 4, wherein both R are sodium.
6. The compound of claim 1, wherein Hal is bromine.
7. The compound of claim 1, wherein Hal is chlorine.
8. A method of treating a disease associated with protein aggregation, the method comprising administering a therapeutically effective amount of a compound of claim 1 to a patient in need thereof wherein the disease is selected from the group consisting of Parkinson's disease, prion disease, Alzheimer's disease, multiple system atrophy, Diffuse Lewy body disease, frontotemporal dementia, amyotrophic lateral sclerosis, Huntington disease's, spinocerebellar ataxias and other Poly-Q diseases, hereditary cerebral amyloid angiopathy, familial amyloid polyneuropathy, primary systemic amyloidosis (AL amyloidosis), reactive systemic amyloidosis (AA amyloidosis), type H diabetes, injection-localized amyloidosis, beta-2 microglobulin amyloidosis, hereditary non-neuropathic amyloidosis, and Finnish hereditary systemic amyloidosis.

9. The method of claim 8, wherein the disease associated with protein aggregation is characterized by the presence of an aggregated form of at least one protein or a fragment or derivative thereof, wherein the protein is selected from the group consisting of prion protein, amyloid precursor protein (APP), alpha-synuclein, superoxide dismutase, tau, immunoglobulin, amyloid-A, transthyretin, beta 2-microglobulin, cystatin C, apolipoproteine A1, TDP-43, islet amyloid polypeptide, ANF, gelsolin, insulin, lysozyme, fibrinogen, huntingtin and ataxin and other proteins with a Poly-Q stretch.

10. The method of claim 8, wherein the prion disease is selected from the group consisting of sporadic and genetic Creutzfeldt-Jakob disease, variant Creutzfeldt-Jakob disease (vCJD), a human disorder caused by the infectious agent of bovine spongiform encephalopathy (BSE), Gerstmann-Sträussler-Scheinker syndrome, fatal familial insomnia, kuru, BSE of cattle, scrapie of sheep and goats, feline spongiform encephalopathy (FSE) of cats, transmissible mink encephalopathy (TME) of minks, exotic ungulate encephalopathy (EUE) of Nyala and Greater Kudu, and chronic wasting disease (CWD) of deer and elk.

11. A composition comprising one of the compounds of isomeric structures Ia and Ib of claim 1, or a mixture thereof and a pharmaceutically acceptable additive.

12. The composition of claim 11, wherein Y is N and Z is —CH—.

13. The composition of claim 11, wherein the compound is

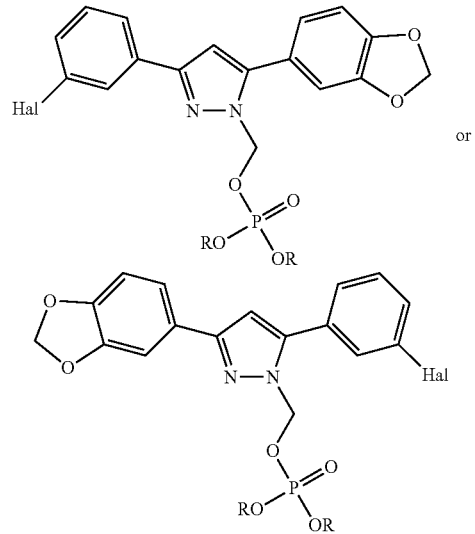

or wherein Hal is a halogen selected from chlorine or bromine, and wherein each R independently is selected from hydrogen, or a cation.

14. The composition of claim 11, wherein at least one R is a cation selected from the group consisting of sodium, lithium, potassium, and ammonium, or protonated forms of ethanolamine, choline, lysine, meglumine, piperazine, and tromethamine.

15. The composition of claim 14, wherein both R are sodium.

16. The composition of claim 11, wherein Hal is bromine.

17. The composition of claim 11, wherein Hal is chlorine.

18. The composition of claim 11, comprising a mixture of a compound having structure Ia and a compound having structure Ib.

* * * * *